United States Patent
Kuno et al.

(10) Patent No.: US 6,682,763 B2
(45) Date of Patent: Jan. 27, 2004

(54) SKIN-BEAUTIFYING AGENT, ANTI-AGING AGENT FOR THE SKIN, WHITENING AGENT AND EXTERNAL AGENT FOR THE SKIN

(75) Inventors: Noriyasu Kuno, Yokosuka (JP); Miho Matsumoto, Zushi (JP)

(73) Assignee: The Nisshin Oil Mills, Ltd., Tokyo (JP)

( * ) Notice: Subject to any disclaimer, the term of this patent is extended or adjusted under 35 U.S.C. 154(b) by 0 days.

(21) Appl. No.: 10/114,107

(22) Filed: Apr. 3, 2002

(65) Prior Publication Data

US 2002/0176903 A1 Nov. 28, 2002

Related U.S. Application Data

(63) Continuation of application No. PCT/JP00/07134, filed on Oct. 13, 2000.

(30) Foreign Application Priority Data

Oct. 14, 1999 (JP) ............................................. 11-293038
Oct. 14, 1999 (JP) ............................................. 11-293039

(51) Int. Cl.$^7$ ............................................. A61K 35/78
(52) U.S. Cl. ..................... 424/769; 424/401; 424/777
(58) Field of Search ................................ 424/401, 769, 424/777

(56) References Cited

U.S. PATENT DOCUMENTS 5,242,952 A * 9/1993 Tritsarolis
5,653,966 A * 8/1997 Bertoli et al.

FOREIGN PATENT DOCUMENTS

| JP | 8-119825 A | 5/1996 |
| JP | 11-335233 A | 12/1999 |
| JP | 2000-119155 A | 4/2000 |

OTHER PUBLICATIONS

Derwent English abstract of Japanese Pat. Appl. No. 09078061 A (Mar. 1997).*
Visoli, F. et al., "Waste waters' from olive oil production are rich in natural antioxidants." Experientia 51:32–34 (1995), Basel, Switzerland.

* cited by examiner

Primary Examiner—Leon B. Lankford, Jr.
Assistant Examiner—Susan D. Coe
(74) Attorney, Agent, or Firm—Burns, Doane, Swecker & Mathis, LLP

(57) ABSTRACT

The present invention relates to an external agent for the skin comprising an extract prepared from olive plants and also relates to an external agent for the skin comprising the extract as a skin-beautifying component, in particular, as an ant-aging component for the skin and/or a whitening component. The extract can be prepared by extracting olive plants and/or products generated during and after the olive oil-manufacturing processes with water and/or an organic solvent and further the extract can further be subjected to a concentration treatment and/or a fractionation-purification treatment to thus improve each effect.

Moreover, the present invention also relates to a skin-beautifying agent, in particular, an anti-aging agent and a skin-whitening agent, containing the extract as an effective component.

22 Claims, No Drawings

SKIN-BEAUTIFYING AGENT, ANTI-AGING AGENT FOR THE SKIN, WHITENING AGENT AND EXTERNAL AGENT FOR THE SKIN

This application is a continuation of International Application No. PCT/JP00/07134 filed on Oct. 13, 2000, which International Application was published by the International Bureau in Japanese on Apr. 19, 2001.

BACKGROUND OF THE INVENTION

The present invention relates to an external agent for the skin containing an extract derived from an olive plant (*Olea europaea* L.) and more specifically to an external agent for the skin having a skin-beautifying effect, in particular, an anti-aging effect related to effects of preventing and eliminating the wrinkles and sags of the skin and a whitening effect, which can relieve or lighten and/or prevent the dark skin, melasma, ephelis and darkening or dullness of the skin. In addition, the present invention also relates to a skin-beautifying agent, a whitening agent and an anti-aging agent for the skin, comprising an extract derived from an olive plant as an effective component as well as an external agent for the skin containing the same.

Oils and fats, in particular those containing an unsaturated fatty acid are quite susceptible to oxidation and this accordingly becomes a principal cause of the quality deterioration thereof and the reduction of nutritive properties and functional characteristics of the same. Among the unsaturated fatty acids, linoleic acid, linolenic acid and arachidonic acid play important roles as essential fatty acids and nutritive substances. Moreover, the physiological activities of higher unsaturated fatty acids such as EPA and DHA have attracted special interest recently and foods and beverages rich in these nutritive substances have been put on the market. These unsaturated fatty acids have very low stability to oxidation and therefore, an antioxidant should be incorporated into these foods and beverages containing such fatty acids, but there has not yet been developed any antioxidant effective for storing these products over a long period of time.

The organisms efficiently generate the energy required for survival while making use of oxygen. However, active oxygen species are formed, as intermediates, during the process wherein oxygen is transformed into water in such an energy metabolism. As such kinds of the active oxygen species, there have in general been known, for instance, superoxide anions released by, for instance, the stimulation of macrophages and hydroxy radicals formed through, for instance, the exposure to radioactive rays. These active oxygen species are formed due to external incentives such as irradiation with excess radioactive rays or ultraviolet rays and ingestion of chemical substances or smoking and internal causes such as re-circulation after ischemia, inflammation, stress and aging. The active oxygen species thus excessively formed in the living body in general have a high chemical reactivity, easily react with various components adjacent thereto in the living body such as lipids, nucleic acids and proteins and correspondingly results in oxidative disorders related to a variety of diseases. There has been proved that the superoxide as one of the active oxygen species is closely related to a variety of diseases. For instance, the LDL present in the artery is oxidized by superoxide to form foam cells therein and this in turn becomes a cause of the arterial sclerosis. Moreover, the hydroxy radicals produced through the irradiation with radioactive rays may exert severe lesions on the living body such as carcinogenesis (Halliwell B. & Gutteridge M. C. Biochem. J. 1984, 219: 1–14).

As the toxicity of such active oxygen species to the living body has been proved, antioxidants such as active oxygen species-eliminating substances, having an activity of efficiently eliminating the same are useful as agents for protecting, from the oxidative deterioration, components included in the living bodies or other products such as foods, pharmaceutical agents and agricultural chemicals and the utilitarian use thereof have been expected in, for instance, food industries, in particular, processed marine products, health foods and nutritive foods as well as in the fields of pharmaceutical agents and agricultural chemicals and cosmetics.

Recently, the consumers have been quite sensitive to the safety of not only food additives consisting of chemically synthesized products, but also the antioxidants. For instance, there has been such a tendency that the use of chemically synthesized antioxidants such as BHA (butyl hydroxy anisole) and BHT (butyl hydroxy toluene) is avoided. Moreover, most of other antioxidants such as tocopherols derived from plant oils are lipophilic (non-hydrophilic) in nature and various limitations are often imposed on the practical use thereof.

Under such circumstances, there have conventionally been proposed a variety of antioxidants mainly extracted from naturally occurring raw materials and there has been investigated various applications thereof. Examples of such antioxidants are superoxide dismutase (SOD), which is an enzyme protein, for those possessing the ability of eliminating superoxide; and mannitol, tryptophane and formic acid for those having a hydroxy radical-elimination activity (see, for instance, OYAGI Yoshihiko, "SOD and Active Oxygen Species-Controlling Agents—Their Pharmacological Actions and Clinical Applications", pp. 224 to 228, published by Nippon IGAKU-KAN Publishing Company, 1989).

However, the SOD is an enzyme protein and therefore, it has a poor stability to, for instance, heat. Further, if it is orally administered, almost whole of the administered enzyme is digested and externally excreted and accordingly, the efficacy thereof is thus quite low. On the other hand, there has been developed or proposed only a few practically useful hydroxyl radical-elimination agents, which can efficiently eliminate hydroxyl radicals. For this reason, it is quite difficult, at present, to industrially and stably obtain these antioxidants in large quantities. In this respect, the foregoing SOD is in general effective only for the elimination of superoxide and it has no effect in the elimination of hydroxyl radicals. Similarly, mannitol cannot eliminate superoxide at all.

As raw materials derived from naturally occurring products and having an antioxidant effect, whose development has eagerly been demanded by the consumers, there have been known, for instance, a water-soluble extract derived from defatted lees of sesame seeds as a water-soluble antioxidant component present in the sesame seeds (see, for instance, Japanese Examined Patent Publication (hereunder referred to as "J.P. KOKOKU") No. Sho 61-26342). Moreover, it has also been well known that this extract from the defatted lees includes lignan glycosides and that the lignan glycosides possess a strong hydroxyl radical-elimination activity (see, for instance, Japanese Un-Examined Patent Publication (hereunder referred to as "J.P. KOKAI") No. Hei 8-208685). However, the superoxide-elimination activity of these lignan glycosides included in the sesame seeds is not so high.

Under such circumstances, there has been desired for the development and stable supply of effective components derived from naturally occurring products having not only an elimination activity for only one kind of active oxygen species, but also a strong elimination activity for several kinds of active oxygen species such as the combination of superoxide and hydroxy radicals, but only a few such effective components have been commercially put on the market. Moreover, almost no effective component having both of such elimination activities has been supplied and therefore, there has been desired for the stable supply of such components.

On the other hand, as cosmetics for imparting the tenseness and gloss to the skin and for preventing the occurrence of wrinkles and sags thereof or those for preventing the so-called aging of the skin, various types of products have been proposed. Typical examples thereof include cosmetics, which comprise a moisturizing component such as a polyhydric alcohol (such as glycerin and sorbitol), hyaluronic acid, collagen, elastin, a natural moisturizing factor (such as amino acids, lactic acid salts, sodium pyrrolidone carboxylate and urea), an intercellular lipid (such as sphingolipids, phospholipids, cholesterol), a simulant of lipid (such as olive oil, jojoba oil and squalane); and cosmetics, which comprise a cell-activating component, for instance, a vitamin such as vitamin A, vitamin C, vitamin E or a derivative thereof, vitamin F (linoleic acid) or vitamin H (glutathione), a hormone, a plant extract (glycyrrhetic acid and β-carotene), an animal extract (such as placenta liquid and royal jelly). In addition, cosmetics containing surface-treated titanium powder and/or talc powder for making the melasma and wrinkles of the skin inconspicuous likewise fall within this category.

In general, it has been recognized that the qualitative and quantitative changes of constitutive components in the dermal tissues of the skin may greatly affect the aging of the skin and they result in the formation of wrinkles and sags on the skin serving as a measure for the skin aging. More specifically, the dermal tissue comprises two kinds of fibrous protein components or collagen fibers and elastic fibers (elastin). These protein components undergo modification under a variety of external and internal causes and this may in turn lead to the reduction of the elasticity thereof and wrinkles and sags may correspondingly be formed.

The crosslinks between collagen fibers has been considered to be one of these causes of the foregoing protein modification. This crosslink is important in the infant and younger generation and is promoted by a crosslinking enzyme. However, the crosslinks, which are not needed for the living body, are formed between collagen fibers independent of any crosslinking enzyme even after the complete growth. At present, it has been known that active oxygen is involved in this crosslink-production step (see, for instance, HIROSE Suberu et al. J. Soc. Cosmet. Chem. Japan, 1993, Vol. 26, No. 4, pp. 289–294).

Collagen is produced in the fibroblast cells and decomposed by the action of the enzyme produced by the fibroblast cell per se. The amount of collagen may be maintained at an appropriate level in the tissue, due to the balance between the production and decomposition thereof, but it has been known that the amount of collagen is considerably reduced in the skin tissues existing in the sunlight-exposed area or the so-called light-aged skin. In this respect, OKADA et al. report such findings that active oxygen acts on fibroblast cells to thus reduce the collagen-producing ability thereof and that the active oxygen further promotes the ability of decomposing collagen and as a result, they suggest that the collagen content in the skin composition is reduced due to the influence of the active oxygen (OKADA Tomio, Bulletin of KOSHO-KAI, 1993, Vol. 17, No. 4, pp. 202–206).

In addition, the space between the foregoing fibrous components is occupied by inter-tissue substrates or mucopolysaccharides (mainly consisting of hyaluronic acid). In this respect, however, it has been known that if active oxygen acts on the mucopolysaccharides, a phenomenon takes place, in which the latter is fragmented (into low molecular weight fragments) (KASHIMURA Naoki, "Active Oxygen", pp. 464–468, KYORITSU Publishing Company, 1990).

In this regard, active oxygen species include, for instance, superoxide ($O_2^-$), singlet oxygen ($^1O_2$), hydroxyl radicals (.OH) and hydrogen peroxide ($H_2O_2$). It has been considered that among these species, the hydroxyl radical has a high reactivity and shows the highest effect of damaging organisms. In connection with this, TANAKA et al. have investigated the effect of inhibiting any crosslinking of collagen by the use of an experimental system in which collagen and glucose take place a Maillard reaction to thus crosslink the collagen and by the addition of a variety of active oxygen-elimination agents to this system. As a result, they recognize that the elimination agent comprising superoxide or singlet oxygen never shows such a crosslinking-inhibitory effect, while a hydroxyl radical-elimination agent possesses such collagen crosslinking-inhibitory effect. At the same time, they have also investigated any influence of a variety of active oxygen species on the fragmentation of hyaluronic acid and they recognize that hydroxyl radicals show the highest effect (TANAKA Hiroshi et al. Bulletin of KOSHO-KAI, 1993, Vol. 17, No. 4, pp. 207–213).

It has been well known that the active oxygen is closely related to the oxidation of biological components and the aging of living bodies as a principal cause thereof and the skin is also affected by the active oxygen like other internal organs. The skin is always exposed to the external world and is a site always exposed to strong oxidation stress. For this reason, the skin is provided with a variety of protective mechanisms against these continuous oxidation stresses. For instance, the horny layer plays a role of physically protecting the skin from light rays such as reflection, absorption and scattering ultraviolet rays and the epidermis includes a variety of biological antioxidants represented by superoxide dismutase (SOD) in order to eliminate active oxygen species produced. For instance, it has been known that tryptophane as one of amino acids generates superoxide through the irradiation with ultraviolet rays, but it is inactivated due to the action of the biological SOD. The progress of various oxidation reactions is thus inhibited in advance under the usual conditions. If this protective mechanism is impaired by any abnormal oxidation stress such as excess sunburn, however, this not only becomes a cause of dermatitis, excess of pigments and skin cancer, but also induces various phenomena such as the aging of the skin because of continuous oxidation stress.

As has been discussed above, it would be recognized that the prevention of the generation of any active oxygen and the removal of such active oxygen are effective for controlling the aging of the skin such as the formation of wrinkles and/or sags. However, there have been known only mannitol, tryptophane, thiourea, formic acid, alcohols or the like as hydroxyl radical-elimination agents and there has not yet been developed any hydroxyl radical-elimination agent, which is practically effective in a trace amount and therefore, it is quite difficult to commercially and stably obtain such an agent in a large amount, under the existing circumstances.

Furthermore, the dark skin and the melasma and ephelis of the skin are caused according to the mechanism detailed below: In general, the melanocyte is activated due to the stimulation by the irradiation with ultraviolet rays in the sunlight, the abnormality in the hormone balance or genetic causes and as a result, the melanin pigment produced by the melanocyte is abnormally deposited in the skin. There have been developed whitening agents such as L-ascorbic acid or derivatives thereof, hydroquinone derivatives, glutathione and colloidal sulfur, for the purpose of eliminating or preventing such abnormal deposition of melanin pigments. However, problems arise such that these whitening agents include those having only a weak melanin production-inhibitory function, those quite susceptible to oxidation and unstable and those giving out bad smells or forming precipitations. Therefore, if they are used alone in cosmetics, the whitening effect of each resulting product is not always sufficient. Accordingly, there has presently been desired for the development of a whitening agent, which is highly effective, safe and stable, which can eliminate or prevent the occurrence of dark skin and the formation of melasma, ephelis and dullness on the skin or which has an effect of whitening the skin.

On the other hand, there has been known an olive plant belonging to the genus Olive of the family Oleaceae as one of the famous plants whose fruits have been utilized from ancient times. The olive is a plant, which has been grown from old times and the representative olive-growing area is, at present, the district along the shore of the Mediterranean. Regarding the applications thereof, the olive oil among others is highly valued and has widely been used in not only the Europe, but also various countries in the world including Japan and the United States. The olive oil has been known to have a variety of effects and has empirically been used in drugs or cosmetics from old times. Moreover, the fruits of the olive plant have been eaten without any treatment and they are optionally salted for use as one of keepable foods. For this reason, the olive fruits are stably available and may be vegetable raw materials having high safety to the human body. However, the olive oil seedcakes, remaining after pressing olive oil from the olive seeds, have simply been used as a fertilizer or a fuel.

It has recently been know that the olive oil is one relatively unsusceptible to oxidation, polyphenols included therein as trace components have attracted special interest and there have been conducted various studies to elucidate, for instance, the physiological functions thereof (see, for instance, International Olive Oil Council. New Food Industry, 1992, Vol. 34, No. 4, pp. 28–52). However, there has not yet been reported much information on the olive, other than the olive oil. In particular, it has not been known that components extracted from the olive plant possess a strong active oxygen-elimination function and an excellent melanin production-inhibitory function and that an external agent for the skin containing the extract has skin-beautifying effects such as an excellent whitening effect and an effect of resisting the aging of the skin.

DISCLOSURE OF THE INVENTION

An object of the present invention is to provide an external agent for the skin, which has a skin-beautifying effect, in particular, an anti-aging effect for the skin or an effect of imparting tenseness and gloss to the skin and eliminating or preventing such aging of the skin as the formation of, for instance, wrinkles and/or sags, which has an excellent whitening effect or an effect of eliminating or preventing the occurrence of any dark skin and the formation of melasma, ephelis and dullness and which is stable and safe for the human body. Another object of the present invention is to provide a skin-beautifying agent, a whitening agent and an anti-aging agent, which have the same excellent effects discussed above in connection with the external agent for the skin.

The inventors of this invention have conducted various studies to achieve the foregoing objects of the present invention, have found that an external agent for the skin comprising an extract derived from olive plants has a skin-beautifying effect, in particular, an anti-aging effect for the skin or an effect of imparting tenseness and gloss to the skin and eliminating or preventing such aging of the skin as the formation of, for instance, wrinkles and/or sags and that it further has an excellent whitening effect or an effect of eliminating or preventing the occurrence of any dark skin and the formation of melasma, ephelis and dullness and have thus completed the present invention.

Accordingly, the present invention relates to an external agent for the skin comprising an extract derived from olive plants and preferably an external agent for the skin comprising an extract derived from olive plants as a skin-beautifying component as well as an external agent for the skin comprising an extract derived from olive plants as a whitening component and/or a anti-aging component for the skin. In addition, the present invention relates to an external agent for the skin comprising (A) the following component and (B) at least one member selected from the group consisting of the following drugs:

(A) An extract obtained from olive plants;
(B) Whitening agents, antioxidants, anti-inflammatory agents, cell activators, UV-screening agents, blood circulation-promoters and humectants.

In this respect, the extract can be prepared by extracting olive plants and/or a product obtained in the olive oil-producing process with water and/or an organic solvent and the resulting extract may be subjected to a concentration treatment and/or a fractionation-purification treatment to thus strengthen the foregoing effects of the extract.

The present invention also relates to a skin-beautifying agent comprising, as an effective component, an extract derived from olive plants. This agent can directly be applied to the desired site on the skin or may be used as a raw material for an external agent for the skin. In this respect, the extract can be prepared by extracting olive plants and/or a product obtained in the olive oil-producing process with water and/or an organic solvent and the resulting extract may be subjected to a concentration treatment and/or a fractionation-purification treatment to give a skin-beautifying agent whose effects are further improved.

Moreover, the present invention relates to a whitening agent comprising, as an effective component, an extract derived from olive plants. This agent can directly be applied to the skin for the purpose of whitening the same or may be used as a raw material for an external agent for the skin. In this respect, the extract can likewise be prepared by extracting olive plants and/or a product obtained in the olive oil-producing process with water and/or an organic solvent and the resulting extract may be subjected to a concentration treatment and/or a fractionation-purification treatment to give a whitening agent whose effects are further improved.

The present invention further relates to an anti-aging agent comprising, as an effective component, an extract derived from olive plants. This agent can likewise directly be applied to the desired site on the skin or may be used as a raw material for an external agent for the skin. In this respect, the extract can likewise be prepared by extracting olive plants and/or a product obtained in the olive oil-producing process with water and/or an organic solvent and the resulting extract may be subjected to a concentration treatment and/or a fractionation-purification treatment to give an anti-aging agent whose effects are further improved.

In addition, the present invention also relates to an external agent for the skin comprising the foregoing skin-beautifying agent and preferably an external agent for the skin comprising the foregoing skin-beautifying agent and/or the foregoing anti-aging agent.

The present invention further relates to an extract having a whitening effect and prepared from olive plants.

Moreover, the present invention likewise relates to an extract having an anti-aging effect for the skin and prepared from olive plants.

BEST MODE FOR CARRYING OUT THE INVENTION

The present invention will hereunder be described in more detail.

The present invention relates to an external agent for the skin comprising an extract obtained mainly from the fruits or seeds, or further from the pericarp, seed coat, leaves, stems and buds of the olive plant as well as the dried products, pulverized products and defatted products thereof. The resulting extract possesses strong active oxygen-elimination function, in particular, an active oxygen-elimination function such that it can simultaneously and effectively eliminate superoxide and hydroxyl radicals and has quite excellent melanin-production-inhibitory function, but the external agent for the skin shows a skin-beautifying effect, in particular, an anti-aging effect for the skin or an effect of imparting tenseness and gloss to the skin and eliminating or preventing such aging of the skin as the formation of, for instance, wrinkles and/or sags and the agent has an excellent whitening effect or an effect of eliminating or preventing the occurrence of any dark skin and the formation of melasma, ephelis and dullness, since the agent comprises the foregoing extract.

The extract used in the external agent for the skin according to the present invention can be obtained from olive plants and, in particular, it is suitably produced from the fruits and/or seeds of the olive plant. Moreover, the extract prepared from the defatted fruits and/or seeds of the olive plant is preferred in the present invention, since the extract does not require any process for removing unnecessary oil components or the like.

The term "olive plant(s)" herein used includes products obtained during the olive oil-manufacturing processes such as residues obtained after pressing, residues remaining after extraction, pressed oils, extracted oils, oil sludge obtained after de-gumming, oil sludge obtained after removal of acids, dark oils, waste decolorizing agents, scum obtained after deodorization, juice obtained by oil expression, waste water and waste filtering materials. For instance, the extract used in the present invention can likewise be obtained from not only lees (or seedcakes) obtained after oil expression such as residues obtained after pressing and residues remaining after extraction, but also oil sludge and waste water produced during the olive oil expression process, which has in general been discarded. These embodiments are preferred from the viewpoint of effective use of the olive plant.

The external agent for the skin according to the present invention is one containing an extract derived from olive plants, one containing the extract as a skin-beautifying component and, in particular, one containing the same as a whitening component and/or an anti-aging component for the skin. The present invention also relates to an external agent for the skin characterized in that it comprises the extract and at least one member selected from the group consisting of whitening agents, antioxidants, anti-inflammatory agents, cell activators, UV-screening agents, blood circulation-promoters and humectants. The extract used in the external agent for the skin according to the present invention possesses a strong active oxygen-elimination function such as an excellent superoxide-elimination activity and an excellent hydroxyl radical-elimination activity and a strong melanin-production-inhibitory function. Accordingly, the external agent for the skin containing the extract has a skin-beautifying effect and, in particular, an excellent whitening effect and/or an excellent anti-aging effect for the skin. Moreover, as a result of the foregoing functions, the extract may impart an antioxidant effect to the external agent for the skin. For instance, the storage properties of the agent are improved. In other words, the external agent for the skin of the present invention is one containing an excellent natural component, in particular, a component having a skin-beautifying effect. Moreover, the external agent for the skin of the present invention comprises a component having a skin-beautifying effect, in particular, a whitening effect and an anti-aging effect for the skin and this agent accordingly has a whitening effect for eliminating and preventing the occurrence of any dark skin and the formation of melasma, ephelis and dullness caused due to the abnormal deposition of melanin pigments synthesized by the melanocytes activated by, for instance, stimulation such as irradiation of the skin with ultraviolet rays, abnormality in the hormone balance or metabolism or genetic causes, as well as an anti-aging effect for the skin or an effect of eliminating and preventing the occurrence of any wrinkle or sag. The amount of the extract to be incorporated into the external agent for the skin is not restricted to any particular level and the agent may comprise the extract in an amount appropriately selected depending on the desired levels of every effects expected by the external agent for the skin.

Moreover, the present invention also relates to an external agent for the skin containing an extract obtained by extracting, for instance, the foregoing olive plants with water and/or an organic solvent and the present invention preferably relates to an external agent for the skin, which comprises an extract obtained by the foregoing extraction procedures wherein the organic solvent is preferably a hydrophilic organic solvent and more preferably the hydrophilic organic solvent is an alcohol.

The extract included in the external agent for the skin of the present invention has an excellent active oxygen-elimination function. Moreover, the extract can be prepared in a high yield per unit mass of the raw material. From the foregoing two facts, it is found that the extract has a value of the strength of the activated oxygen-elimination function multiplied by the yield per unit mass of the raw material, which is defined to be an activated oxygen-elimination function-yield index, substantially higher than those observed for the extracts obtained using other natural raw materials. Regarding the superoxide-elimination activity, the activated oxygen-elimination function-yield index is not less than 100 and approximately ranges from about 100 to 3250 for the extract obtained per unit mass of the raw material.

For instance, the index is high on the order of 1 to 650 times that observed for the extract obtained from sesame. Thus, the present invention would permit the production of such an extract having a strong antioxidant effect and a strong anti-aging effect for the skin in a high yield.

In addition, the extract possesses an excellent melamine-production-inhibitory function, which is identical to or superior to that observed for arbutin as a known whitening agent. If using arbutin as a positive control, the resulting relative index of the melamine-production-inhibitory function of the extract is about 0.5 to 5 times that observed for arbutin, even in case of a crude extract. Further, the index ranges from about 10 to 50 when the crude extract is subjected to a concentration treatment and/or a fractionation-purification treatment and this indicates that the extract has a quite high melanin-production-inhibitory function. Moreover, the extract has a cytotoxicity to B-16 melanoma cells considerably lower than that observed for arbutin and therefore, it would be concluded that the extract has a quite low toxicity to the skin. In other words, the extract is less toxic to the cells as compared with arbutin and therefore, it can, for instance, be applied to the skin in an amount greater than those of the existing whitening agents. Therefore, the whitening effect expected when the extract is practically applied to the skin would be higher than that observed for arbutin or the like. The substantial index of the melanin-production-inhibitory function for the extract, which is defined, while taking into consideration the skin-whitening effect and the amount actually applicable to the skin ranges from about 1 to 10 for the crude extract and it ranges from about 10 to 50 for the extract obtained by subjecting the crude extract to a concentration treatment and/or a fractionation-purification treatment, as compared with arbutin. This clearly indicates that the extract can, indeed, exert a high whitening effect on the skin. Moreover, this fact means that the extract can be incorporated into, for instance, cosmetics in a high concentration and therefore, the cosmetics or the like containing the extract can ensure a high skin-whitening effect.

Further, the extract is preferably one subjected to a concentration treatment and/or a fractionation-purification treatment. The concentration treatment may be, for instance, a treatment for recovering a soluble fraction and/or an insoluble fraction, which makes use of the solubilities of components in water and/or an organic solvent; a liquid—liquid partition treatment using a mixed water-hydrophobic organic solvent system; a recrystallization treatment; a re-precipitation treatment; and a treatment for recovering precipitates formed upon cooling. The fractionation-purification treatment usable herein is, for instance, a recrystallization treatment; a re-precipitation treatment; purification by the normal phase and/or reverse phase chromatography; a discoloring treatment; and/or a deodorization treatment. Accordingly, the present invention also relates to a discolored and/or deodorized extract having a whitening effect or an anti-aging effect for the skin.

The foregoing treatment such as the concentration-purification treatment permits the improvement of the functions of the extract such as the active oxygen-elimination function and melamin-production-inhibitory function and this in turn improves the secondary effects such as the skin-beautifying effect, whitening effect, anti-aging effect for the skin and antioxidant effect of the extract. For instance, if the extract is concentrated by the method, which makes use of the solubilities of components in water, the resulting concentrated extract may have a skin-whitening effect several times greater than that of the crude extract. For instance, the index of the melanin-production-inhibitory function (relative to the value of arbutin as a reference) of the resulting extract ranges from 8 to 20 and this indicates that the extract has a skin-whitening effect considerably higher than that observed for arbutin. In addition, the extract may be subjected to a further fractionation-purification treatment to further improve each effect thereof and may likewise be subjected to a further discoloration-deodorization treatment to give a colorless and odorless extract and to thus improve the applicability thereof. In this case, the extract can be used in a wide variety of fields and a wide variety of applications since it is not limited in the color and/or odor.

The combination of an extraction treatment and a concentration treatment and/or a purification treatment is not restricted to any specific one. For instance, the olive plant is extracted with water and/or a hydrophilic organic solvent, a part or the whole of the hydrophilic organic solvent is removed from the resulting extract and then the insolubles precipitated in the aqueous phase is recovered to concentrate the extract. The precipitated water-insolubles can be recovered by, for instance, filtration or centrifugation, but optionally water can be added to the aqueous solution with or without stirring to improve the rate of recovery. Moreover, the dried extract obtained by the removal of the water and/or the hydrophilic organic solvent from the extract derived from the olive plant can be subjected to a water-addition treatment and stirring treatment and then the resulting water-insolubles are recovered through filtration to thus concentrate the same, as has been described above. These concentrates can be fractionated and/or purified by the normal phase and/or reverse phase chromatography and/or the recrystallization.

In addition, the present invention also relates to a skin-beautifying agent, in particular, a whitening agent and/or an anti-aging agent, comprising an extract derived from olive plants, which is preferably subjected to concentration and/or fractionation-purification treatments as an effective component. Each effect of the extract or agents can be enhanced or controlled by appropriately adjusting the conditions for the concentration and/or fractionation-purification treatments. The skin-beautifying, whitening and anti-aging agents may directly be applied to the skin for achieving the desired effects, or may be used as a raw material for the external agent for the skin.

The present invention further relates to an external agent for the skin comprising the foregoing skin-beautifying agent and an external agent for the skin comprising the foregoing whitening agent and/or the anti-aging agent. The external agent for the skin possesses effects identical to those observed for the foregoing external agent for the skin.

In this respect, the extract is derived from olive plants. Therefore, the extract is excellent in the safety for the human body and the skin and the stable supply thereof can be ensured since the olive is one of the quite common plants.

The olive plant (*Olea europaea* L.) used in the invention as a raw material may be any one irrespective of the habitats and may thus be those home-grown or Europe growth or may be edible ones or those for the oil expression. The extract used in the external agent for the skin according to the present invention can be obtained mainly from the fruits or seeds, or further from the pericarp, seed coat, leaves, stems and buds of the olive plant as a naturally occurring plant. The extract may likewise suitably be prepared from the dried products, pulverized products and defatted products of the foregoing raw materials.

Moreover, water is preferably added to the foregoing fruits of the olive plant or the defatted product thereof or the fruits or the defatted product thereof are humidified by a steaming treatment. Thus, they appropriately get swollen and therefore, the extraction efficiency is improved.

In particular, the defatted product of the olive plant includes substances to be extracted in high concentrations. Accordingly, it is preferred to obtain the desired extract from the defatted product since the extract can be prepared in a very high yield and it is not necessary to remove the oil fraction from the resulting extract. Therefore, the present invention also relates to an extract derived from olive plants and having a whitening effect or an anti-aging effect for the skin.

In addition, it is also possible to use a defatted product obtained when the lipid components contained in the olive plant or the defatted product thereof are removed by extraction with at least one member selected from the group consisting of hydrocarbons such as pentane, hexane and heptane, lower alkyl fatty acid esters such as ethyl ester of acetic acid and known water-insoluble organic solvents such as diethyl ether and further the foregoing washing operation is if necessary repeated.

Extracting olive plants with water and/or an organic solvent can prepare the extract used in the external agent for the skin of the present invention. Preferably, the extract having a whitening or anti-aging effect for the skin according to the present invention can be prepared from the olive plants using at least one member selected from the group consisting of water, water-containing alcohols, anhydrous alcohols, acetone, tetrahydrofuran and acetonitrile.

The organic solvent used for obtaining the extract, from the olive plants, which is incorporated into the external agent for the skin according to the present invention may be either a hydrophilic organic solvent or a hydrophobic organic solvent. Specific examples of the hydrophilic organic solvents are primary alcohols such as methyl alcohol, ethyl alcohol, 1-propanol and 1-butanol, secondary alcohols such as 2-propanol and 2-butanol, secondary alcohols such as 2-methyl-2-propanol, liquid polyhydric alcohols such as ethylene glycol, glycerin, propylene glycol and 1,3-butylene glycol, and other known organic solvents such as acetone, tetrahydrofuran, acetonitrile, 1,4-dioxane, pyridine, dimethylsulfoxide, N,N-dimethyl formamide and acetic acid. In addition, specific examples of the hydrophobic organic solvents are known organic solvents such as hexane, cyclohexane, carbon tetrachloride, chloroform, dichloromethane, 1,2-dichloroethane, diethyl ether, ethyl acetate, benzene and toluene. These organic solvents may be used alone or in any combination of at least two of them.

The use of water and/or a hydrophilic organic solvent is preferred from the industrial standpoint, for instance, from the viewpoint of the permeability thereof into the plant's tissues and the extraction efficiency and it is also preferred to use water-containing hydrophilic organic solvents. Specific examples thereof include alcohols such as methyl alcohol, ethyl alcohol, glycerin, propylene glycol and 1,3-butylene glycol, other organic solvents such as acetone, tetrahydrofuran and acetonitrile and these solvents containing water. The extract used in the external agent for the skin according to the present invention can be obtained from the olive plant using at least one member selected from the group consisting of the solvents listed above.

More preferably, the olive plant is extracted with water, water-containing lower alcohols or anhydrous lower alcohols.

If the extract having an active oxygen-elimination function is prepared, while making use of the solubility characteristics of the extract component possessing various functions, it is preferred to conduct the extraction procedures using water and/or a hydrophilic organic solvent, preferably a water-containing hydrophilic organic solvent and more preferably a water-containing hydrophilic organic solvent having a high water content.

In addition, an extract having a melanin-production-inhibitory function is preferably prepared by the extraction with water and/or a hydrophilic organic solvent, preferably a water-containing hydrophilic organic solvent and more preferably a water-containing hydrophilic organic solvent having a high water content. Alternatively, it is also possible to use a hydrophobic organic solvent and a solvent comprising a specific combination of solvents and having an improved ability of solubilization.

The conditions for the extraction are not restricted to any specific one and the extraction can, for instance, be conducted at a temperature ranging from 5 to 95° C., preferably 5 to 60° C., more preferably 10 to 90° C. and further preferably 15 to 85° C. Moreover, the extraction can likewise suitably be conducted at ordinary temperature. There is such a tendency that the higher the extraction temperature, the higher the extraction efficiency. The extraction may suitably be carried out at ordinary pressure, under pressure or a reduced pressure established by, for instance, aspiration. Moreover, the extraction may be carried out by the shaking extraction technique or by the use of an extraction device equipped with, for instance, a stirring machine, in order to improve the extraction efficiency. The extraction time may vary depending on other extraction conditions, but in general ranges from several minutes to several hours. In this respect, the longer the extraction time, the higher the extraction efficiency. However, the extraction time may appropriately be determined or selected depending on the production conditions such as production facilities and yields.

In addition, the amount of the solvent used in the extraction ranges from 1 to 100 times (mass/mass) and preferably 1 to 20 times that of the raw material.

The solvent used in the extraction is preferably water and/or a hydrophilic organic solvent and more preferably a water-containing hydrophilic organic solvent while taking into consideration the yield of the resulting extract and methods for recovering the extract after the extraction procedures. In particular, it is preferred to use a water-containing alcohol and more preferably a water-containing lower alcohol.

If the extraction process is carried out using a water-containing hydrophilic organic solvent, it is preferred to carry out the extraction with a water-containing hydrophilic organic solvent whose content of the hydrophilic organic solvent ranges from 10 to 95% by mass, the water-containing hydrophilic organic solvent more preferably has a content of the hydrophilic organic solvent ranging from 20 to 95% by mass and the solvent most preferably has a content of the hydrophilic organic solvent ranging from 30 to 95% by mass.

If the extraction is conducted using a water-containing hydrophilic organic solvent and the intensity of the active oxygen-elimination function of the resulting extract is also taken into consideration, the extraction is preferably carried out using a water-containing hydrophilic organic solvent whose content of the hydrophilic organic solvent is not less than 10% by mass, more preferably a water-containing hydrophilic organic solvent whose content of the hydrophilic organic solvent is not less than 40% by mass and most preferably a water-containing hydrophilic organic solvent whose content of the hydrophilic organic solvent is adjusted to the range of from 40 to 80% by mass.

Moreover, if taking into consideration the intensity of the melanin-production-inhibitory function of the resulting extract, preferably used in the extraction with a water-containing hydrophilic organic solvent are those having a content of the hydrophilic organic solvent of not less than 10% by mass, more preferably those having a content of the hydrophilic organic solvent ranging from 10 to 95% by mass and most preferably those having a content of the hydrophilic organic solvent adjusted to the range of from 30 to 95% by mass.

Moreover, it is preferred to carry out the extraction using either of water, a water-containing lower alcohol or an anhydrous lower alcohol if taking into consideration the safety for the human body when it is applied to the skin. In addition, it is also preferred to use water and/or an alcohol in the extraction.

Water and/or an alcohol are preferably used and the use of a water-containing alcohol is also preferred from the viewpoint of the yield of the extract and the recovery thereof after the extraction.

Moreover, if the extraction is carried out using a water-containing alcohol, the extraction is preferably conducted using a water-containing alcohol having an alcohol content ranging from 20 to 95% by mass, in particular, a water-containing alcohol having an alcohol content ranging from 20 to 80% by mass and most preferably a water-containing alcohol whose alcohol content is adjusted to the range of from 30 to 95% by mass. In particular, the alcohol is preferably a lower alcohol.

Moreover, if taking into consideration the intensity of the active oxygen-elimination function of the resulting extract, the extraction is preferably carried out using a water-containing alcohol having an alcohol content of not less than 10% by mass. The water-containing alcohol used herein more preferably has an alcohol content of not less than 40% by mass and the alcohol content of the water-containing alcohol is most preferably adjusted to the range of from 40 to 80% by mass. In particular, the alcohol is preferably a lower alcohol.

Furthermore, if taking into consideration the intensity of the melanin-production-inhibitory function of the resulting extract, the olive plant is preferably extracted with a water-containing alcohol having an alcohol content of not less than 10% by mass. The water-containing alcohol used herein more preferably has an alcohol content ranging from 10 to 95% by mass and the alcohol content of the water-containing alcohol is most preferably adjusted to the range of from 30 to 95% by mass. In particular, the alcohol is preferably a lower alcohol.

In this respect, examples of the alcohols used in the present invention are known solvents, for instance, primary alcohols such as methyl alcohol, ethyl alcohol, 1-propanol and 1-butanol, secondary alcohols such as 2-propanol and 2-butanol, tertiary alcohols such as 2-methyl-2-propanol, and liquid polyhydric alcohols such as ethylene glycol, glycerin, propylene glycol and 1,3-butylene glycol. These solvents may be used alone or in any combination of at least two of them.

In particular, it is preferred to use a lower alcohol from the industrial standpoint, for instance, from the viewpoint of production cost and the handling ability such as the removal of the solvent through distillation.

The term "lower alcohol" herein used means a known alcohol having 1 to 4 carbon atoms such as a primary, secondary, tertiary or liquid polyhydric alcohol listed above, which may be used alone or in any combination of at least two of them.

In addition, the term "olive plant" herein used includes products obtained during or after the olive oil-manufacturing processes such as residues obtained after pressing, residues remaining after extraction, pressed oils, extracted oils, oil sludge obtained after de-gumming, oil sludge obtained after removal of acids, dark oils, waste decolorizing agents, scum obtained after deodorization, juice obtained by oil expression, waste water and waste filtering materials. The extract having an active oxygen-elimination function and a melanin-production-inhibitory function and used in the present invention can likewise be obtained from these raw materials. These methods for preparing extracts are preferred from the viewpoint of effective use of the olive plant.

The extract used in the present invention can likewise be obtained from the waste water produced during the olive oil expression process. The resulting extract has not only an active oxygen-elimination function, but also a melanin-production-inhibitory function. In particular, expressing the fruits of the olive plant in the olive oil expression forms an oil fraction and a product called juice containing moisture and then the water is removed from the product to give olive oil. In this respect, the recovery of the precipitates formed in the foregoing aqueous phase can suitably produce an extract having a melanin-production-inhibitory function and a tumor cell-proliferation-inhibitory and/or extinction function.

As has been described above, the extraction using water and/or an organic solvent would permit the preparation of an extract possessing an active oxygen-elimination function and a melanin-production-inhibitory function.

Moreover, the water-soluble components or the like of the extract used in the external agent for the skin according to the present invention are excellent in an antioxidant effect and an anti-aging effect for the skin, while hardly water-soluble and/or oil-soluble fractions thereof have a strong skin-whitening effect.

A dried extract used in the external agent for the skin of the present invention can be obtained by the removal of the solvent and water from the extract thus prepared.

The solvent and the water can be removed according to any known method such as distillation under reduced pressure, drying under reduced pressure or in vacuo, lyophilization (or freeze-drying), and spray drying.

In this respect, it is a matter of course that the extract may be used without removing any such solvent and water or only the solvent is removed from the extract to give an aqueous solution. Moreover, appropriate control of the degree of the removal of the solvent and the moisture would permit the control of the concentration of the extract or the control of the intensities of the active oxygen-elimination function and the melanin-production-inhibitory function and this leads to the preparation of an aqueous solution having controlled active oxygen-elimination and melanin-production-inhibitory functions.

In addition, the production method of the present invention permits the preparation of an extract having, for instance, an active oxygen-elimination function and a melanin-production-inhibitory function in a high yield per unit mass of the raw material as compared with the conventional methods using other natural raw materials. For instance, the method of the invention permits the achievement of a high yield on the order of 1 to 10 times that observed when sesame is used. Therefore, the present invention also relates to a method for preparing such an extract having indexes of melanin-production-inhibitory function and substantial melanin-production-inhibitory function of not less than 5.

Moreover, the extract derived from a defatted product is preferred since it does not contain any oil-soluble component such as triglyceride, sterol and tocopherol and therefore, the extract never requires any step for the removal of these components and any purification step.

In addition, an extract having an active oxygen-elimination function and a melanin-production-inhibitory function can likewise be prepared from the products obtained during or after the olive oil-manufacturing processes such as residues obtained after pressing, residues remaining after extraction, pressed oils, extracted oils, oil sludge obtained after de-gumming, oil sludge obtained after removal of acids, dark oils, waste decolorizing agents, scum obtained after deodorization, juice obtained by oil expression, waste water and waste filtering materials. These methods for preparing extracts from the foregoing raw materials are preferred from the viewpoint of effective use of the olive plant and are also excellent from the viewpoint of the production cost.

These extracts may be used without any post-treatment, but may further be subjected, if necessary, to a concentration treatment and/or a fractionation-purification treatment. The concentrated and purified extract may likewise be used in the present invention.

The concentration treatment is not restricted to any particular one, but it is preferably at least one member selected from the group consisting of a treatment for recovering a soluble fraction and/or an insoluble fraction, which makes use of the solubilities of the components present therein in water and/or an organic solvent; a liquid—liquid partition treatment using a mixed water-hydrophobic organic solvent system; a recrystallization treatment; a re-precipitation treatment; and a treatment for recovering precipitates formed by cooling. In particular, the extract obtained by subjecting it to concentration, while making use of the solubilities of the components present therein in water and/or a fractionation-purification treatment is preferred since it has a strong melanin-production-inhibitory function.

For instance, the use of the concentration method, which makes use of the solubilities of the components present in the extract in water, permits the separation of water-soluble components or the like from those hardly soluble in water and/or insoluble in water or hardly water-soluble components or the like. In this connection, it has been found that the concentrate derived from the water-soluble components has an active oxygen-elimination function higher than that observed for the concentrate derived from the hardly water-soluble components, while the latter has a melanin-production-inhibitory function substantially higher than that observed for the former.

In addition, as an example of the concentration method, a concentrate can easily be obtained in the course of the process for removing the solvent from the extract derived from the olive plant. More specifically, an aqueous solution from which only the solvent has been removed is subjected to, for instance, a filtration treatment, a centrifugation treatment and a decantation treatment to thus separate the water-soluble fraction from the water-insoluble fraction and then these fractions are separately dehydrated and dried to give a concentrate containing, for instance, the water-soluble components and having a strong active oxygen-elimination function and a concentrate containing, for instance, the hardly water-soluble components and having a strong melanin-production-inhibitory function, respectively.

As has been described above, a concentrate having high antioxidant and anti-aging effect for the skins and a concentrate having a high skin-whitening effect can be obtained through a single concentration process and therefore, this concentration method is considered to be a quite excellent means even from the viewpoint of the efficiency.

Alternatively, water is added to the dry product obtained by extracting olive plants and then evaporating the resulting extract to dryness and then the resulting mixture is stirred to thus separate the dry product into components hardly soluble in water and/or insoluble in water or hardly water-soluble components; and components easily soluble in water. This method permits the substantial concentration of the extract. The resulting extract has active oxygen-elimination and melanin-production-inhibitory functions. As has been discussed above, an extract can be separated into components of the extract easily soluble in water or water-soluble components; and components hardly soluble in water and/or insoluble in water or hardly water-soluble components. In this respect, it has been found that the concentrate containing, for instance, the water-soluble components has a high active oxygen-elimination function, while that containing, for instance, the hardly water-soluble components has a considerably high skin-whitening effect.

It has been confirmed that the concentrate containing, for instance, the water-soluble components present in the extract derived from the olive plant has excellent antioxidant and anti-aging effect for the skins considerably higher than those observed for the whole extract from the olive plant and the hardly water-soluble components. In addition, it has also been confirmed that the hardly water-soluble components have an excellent melanin-production-inhibitory function considerably higher than those observed for the whole extract from the olive plant and the concentrate containing, for instance, the water-soluble components present in the extract.

Thus, the concentrate of the water-soluble components and that of the hardly water-soluble components can easily be obtained by adding an extract derived from olive plants to water with stirring and then collecting the separated fraction through, for instance, filtration. Moreover, the amount of the resulting water-soluble components and the intensity of the active oxygen-elimination function can be controlled and the amount of the resulting hardly water-soluble components and the intensity of the melanin-production-inhibitory function can likewise be controlled, by adjusting the amount of water used and the temperature.

Alternatively, the extract used in the external agent for the skin of the present invention can, if necessary, be concentrated by the liquid—liquid partition technique using a combination of currently used solvents. The combination of solvents cannot unconditionally be defined, but examples thereof include combinations of water-hydrophobic organic solvents. Specific examples of such hydrophobic organic solvents are known organic solvents such as hexane, carbon tetrachloride, chloroform, dichloromethane, 1,2-dichloroethane, diethyl ether, ethyl acetate, n-butanol, benzene and toluene.

Regarding this liquid—liquid partition, a concentrate having an active oxygen-elimination function can be obtained by the removal of the water from the aqueous phase, while a concentrate having a melanin-production-inhibitory function can easily be prepared by the removal of the solvent from the organic solvent phase.

Further, the extract and the concentrate thereof can be subjected to a fractionation and/or purification treatment. This permits the concentration of the extract to an extent higher than that attained by the foregoing concentration.

The fractionation and/or purification treatment shows such advantages that the treatment permits the substantial improvement of each effect such as the melanin-production-inhibitory effect and that the treatment permits the removal of impurities presenting the extract. More specifically, the fractionation and/or purification treatment is preferred since the resulting extract can be incorporated into the external agent for the skin of the present invention without undesirably coloring the agent.

The method for the fractionation and/or purification treatment is not restricted to any specific one, but this treatment may suitably be carried out according to, for instance, at least one method selected from the group consisting of purification by normal phase and/or reverse phase chromatography, recrystallization, re-precipitation, discoloring treatments and deodorizing treatments.

Among the chromatography techniques, the liquid chromatography technique is preferably used in the present invention since this technique permits the efficient fractionation and purification without decomposing the components of the extract or concentrate used in the external agent for the skin of the present invention. Specific examples of such liquid chromatography techniques are normal phase liquid chromatography, reverse phase liquid chromatography, thin-layer liquid chromatography, paper chromatography and high performance liquid chromatography (HPLC). Any one of these chromatography techniques may be used in the fractionation-purification treatment of the extract or the concentrate thereof. Preferred are normal phase liquid chromatography, reverse phase liquid chromatography and high performance liquid chromatography (HPLC), while taking into consideration, for instance, the resolution, the loading and the number of steps.

In this connection, the normal phase liquid chromatography means, for instance, the following method. In other words, this method comprises the steps of preparing a column in which the stationary phase comprises, for instance, silica gel and the mobile phase comprises, for instance, a hexane-ethyl acetate mixed liquid or a chloroform-methanol mixed liquid; supplying an extract from olive plants or the concentrate thereof to the column at a rate of loading ranging from 0.1 to 5% (wt (mass)/v (volume)); and then eluting a desired fraction according to the continuous elution method using a single mobile phase or the gradient elution method in which the polarity of the solvent or mobile phase is stepwise increased.

The reverse phase liquid chromatography technique is, for instance, the following method. In other words, this method comprises the steps of preparing a column in which the stationary phase comprises, for instance, silica gel coupled with octadecyl silane (ODS) and the mobile phase comprises, for instance, a water-methanol mixed liquid, a water-acetonitrile mixed liquid or a water-acetone mixed liquid; supplying an extract from olive plants or the concentrate thereof to the column at a rate of loading ranging from 0.1 to 5% (wt (mass)/v (volume)); and then eluting a desired fraction according to the continuous elution method using a single mobile phase or the gradient elution method in which the polarity of the solvent or mobile phase is stepwise increased.

The high performance liquid chromatography (HPLC) technique is, in principle, identical to the foregoing normal phase liquid chromatography and reverse phase liquid chromatography techniques, but is used for the rapid fractionation-purification treatment at a high resolution.

The use of at least one of the foregoing methods is preferred in the present invention since the use thereof would permit the concentration of the extract to a higher extent and the preparation of a concentrate free of any impurity.

The concentration required for achieving each effect can be controlled by the foregoing methods, which are used alone or in any combination of at least two of them and the combination would permit the arbitrary design of the intensity of each effect and characteristic properties of the resulting extract.

The foregoing concentration treatment may be repeated over a desired times or different concentration treatments may be used in combination. Similarly, the fractionation-purification treatment may be repeated over a desired times and different fractionation-purification treatments may be combined. Further, the extract may be subjected to a concentration treatment and then to a fractionation-purification treatment or it may be subjected first to a fractionation-purification treatment and then to a concentration treatment or further it may be subjected to a concentration treatment, a fractionation-purification treatment and a concentration treatment, in this order. Naturally, any combination of these treatments may be used, in addition to the foregoing ones.

Moreover, if a concentrate prepared from the extract derived from the olive plant or the product obtained by further fractionating and/or purifying the concentrate is further subjected to a discoloration and/or deodorization treatment, unnecessary components are removed from the product and the resulting product is colorless or at worst slightly pigmented and/or odorless or almost odorless. Therefore, the resulting product is not restricted in applications due to the color or perfume thereof and accordingly, it may certainly be used in wide variety of fields.

Examples of such discoloration treatments are a treatment with active carbon and a treatment with china clay, while examples of such deodorization treatments likewise include a treatment with active carbon and a treatment with china clay as well as supercritical extraction and steam distillation.

Moreover, an extract having an active oxygen-elimination function and a melanin-production-inhibitory function can likewise be prepared from the products obtained during or after the olive oil-manufacturing processes such as residues obtained after pressing, residues remaining after extraction, pressed oils, extracted oils, oil sludge obtained after de-gumming, oil sludge obtained after removal of acids, dark oils, waste decolorizing agents, scum obtained after deodorization, juice obtained by oil expression, waste water and waste filtering materials. The resulting extract can likewise be subjected to a concentration treatment and/or a fractionation-purification treatment.

The resulting extract and a product obtained by subjecting the extract to a concentration treatment and/or a purification treatment may be used alone or in combination. Thus, the intensities of the active oxygen-elimination function and the melanin-production-inhibitory function can arbitrarily be designed and the resulting product can be used as an extract having further improved active oxygen-elimination and melanin-production-inhibitory functions. Moreover, the extract can be incorporated into other antioxidants, whitening agents and/or carcinostatic agents. Thus, the extract permits any detailed design of the intensity of each effect and the substantial improvement of the function of the extract may be expected because of the synergistic effect with other functional substances.

In addition, these functions may be used in combination. Moreover, the extract has a plurality of functions, the functions may be variously be selected and therefore, the functions of the extract can be designed.

Moreover, the extract can be divided into portions or components having various solubility characteristics while making use of the solubility of each component in water and they can be incorporated into products so as to make the most use thereof.

The component having an active oxygen-elimination function present in the extract used in the external agent for the skin according to the present invention can suitably be incorporated into an aqueous product among others. The extract comprises components easily soluble in water, components hardly soluble in water and those insoluble in water, but as a whole, these components are appropriately dissolved and/or dispersed in water and therefore, the extract can suitably be used in aqueous products. Most of the usual antioxidants such as tocopherols derived from vegetable oils are lipophilic (hydrophobic) by nature and they are largely limited in their practical applications, but the components having an active oxygen-elimination function present in the extract are soluble in water (comprising water-soluble components) and therefore, they can be used in a wide variety of applications and the antioxidants comprising the extract may be recognized as widely used ones.

The extract can favorably be used in a wide variety of aqueous or emulsion type foods and beverages in uniformly dissolved or dispersed conditions.

In particular, regarding the application thereof to cosmetics, the extract can be used in aqueous cosmetics and therefore, the extract is advantageous in that it can be used in cosmetics having a wide variety of applications.

It has been found that the hardly water-soluble components of the extract are excellent, in particular, in the melanin-production-inhibitory function. The hardly water-soluble fraction is preferred since it is excellent in percutaneous absorbability and it can effectively impart its effect to the skin. Regarding the application thereof to oil-based systems, the extract, in particular, the original extract free of any post-treatment comprises relatively large amounts of hardly oil-soluble components and/or oil-insoluble components and therefore, it is preferred to incorporate it into oils and fats after it is purified by, for instance, the removal of insolubles or after water and an emulsifying agent are added to give an emulsion. In particular, if it is intended to impart an active oxygen-elimination function to a product, the extract is preferably subjected to the foregoing treatments.

As has been discussed above, the extract used in the external agent for the skin possesses an active oxygen-elimination function and a melanin-production-inhibitory function.

The term "active oxygen-elimination function" herein used means an ability of, for instance, controlling the generation of active oxygen species and/or catching, eliminating, disproportionating and/or decomposing these species in the living body or foods, pharmaceutical agents and agricultural chemicals. More specifically, examples of such functions are the control of the active oxygen species by chelating and inactivating metal ions, which may induce the formation of such species, the elimination or decomposition of the generated active oxygen species, the disproportionation thereof with, for instance, enzymes and the control and blocking of the radical chain reaction through the catching or stabilization of radicals. In this respect, the term "active oxygen species" mainly means, for instance, superoxide, hydroxy radicals, perhydroxy radicals, hydrogen peroxide and singlet oxygen and also includes peroxides of, for instance, lipids, proteins, carbohydrates and nucleic acids and free radicals derived from the same. These active oxygen species strongly oxidize a variety of components of foods and living bodies such as lipids, proteins, carbohydrates and nucleic acids to thus convert or decompose them into components different from the original ones. Therefore, this function is useful for protecting the components included in, for instance, the living body or an external agent for the skin from any oxidative deterioration. In particular, the extract possesses a high superoxide-elimination activity and a high hydroxy radical-elimination activity, among others.

The term "superoxide-elimination activity" herein used means an ability of disproportionating and inactivating superoxide generated through the mono-electron reduction of oxygen molecules. Superoxide is generated in, for instance, leukocytes and mitochondria in the living body and the formation thereof is inevitable in the living body, which makes use of oxygen. In addition, the superoxide has a relatively low reactivity and can react with limited substances such as iron and nitrogen monoxide. However, it serves as, for instance, a source of hydrogen peroxide, it is thus involved in the formation of other active oxygen species and it may cause oxidative damage of biological components. Accordingly, it is a serious active oxygen species, which should be eliminated immediately after the formation thereof. Superoxide dismutase (SOD) has a superoxide-elimination effect and a biological enzyme included even in the procaryote, but a substance having a superoxide-elimination activity is desirably applied to the living body in order to more positively protect any biological component. However, SOD as an example of such substance is an enzyme protein and has poor stability. For instance, if it is orally administered, most of the same would be excreted and therefore, the efficacy thereof is quite low. In other words, the extract of the present invention can stably show its superonide-elimination activity by the ingestion or application thereof to, for instance, the skin and thus it permits more effective protection of biological components and it in turn contributes to the maintenance of healthy bodies and beautiful skin.

The extract of the present invention is a simple extract, but possesses a superoxide-elimination activity stronger than that observed for BHA having a strong superoxide-elimination function as a synthetic antioxidant. Therefore, the extract can be used not only as a superoxide-elimination agent and lipid-peroxidation-inhibitory agent, but also an antioxidant within the living body (bio-antioxidant).

The term "hydroxyl radical-elimination activity" herein used means the activity or ability of catching and/or stabilizing hydroxyl radicals generated due to various causes. The formation of hydroxyl radicals is inevitable in the life-maintaining behavior of the living things, which makes use of oxygen, the hydroxyl radicals are highly reactive chemical species among a variety of active oxygen species and are active oxygen species having the highest toxicity to such an extent that they may cause oxidative damage of any biological component. An example of the hydroxy radical-producing routes is Fenton's reaction in which iron ions present in the living body are involved in the formation of hydrogen peroxide and superoxide. However, there is not any effective mechanism of eliminating hydroxy radicals and therefore, it is essential to ingest a substance having a hydroxy radical-elimination activity. As such hydroxy radical-elimination agent, there have been known mannitol, tryptophane and formic acid. However, most of these elimination agents should be used in a high concentration although they are single component substances. On the other hand, the extract of the present invention shows its hydroxy radical-elimination activity through the ingestion thereof or the application thereof to, for instance, the skin and accordingly, it permits more effective protection of biological components and it in turn contributes to the maintenance of healthy bodies and beautiful skin.

The extract of the present invention as an extract free of any post-treatment (original extract) would permit the hydroxy radical-elimination (for instance, the inhibition of any peroxidation of linoleic acid) in a considerably small amount and is thus quite effective as compared with the usual hydroxy radical-elimination agents. The extract can thus be used as a hydroxy radical-elimination agent, a lipid-peroxidation-inhibitory agent and may likewise be used as an antioxidant in the living body (bio-antioxidant) and an antioxidant, which can improve the storage stability of any product such as foods, beverages, cosmetics, pharmaceutical agents and feeds.

Moreover, the foregoing SOD is simply effective for eliminating superoxide, does not show any activity of eliminating hydroxy radicals and mannitol cannot likewise eliminate any superoxide. Contrary to this, the extract of the present invention shows an effect of eliminating both of these substances.

More specifically, the extract of the present invention possesses a strong superoxide-elimination activity and a high hydroxy radical-elimination activity or shows an active oxygen-elimination activity against both of these active oxygen species. Thus, the extract can be used in a wide variety of applications.

Regarding the effects, the extract possesses an active oxygen-elimination function or the both superoxide-elimination and hydroxy radical-elimination activities and therefore, it is excellent in the bio-antioxidant effect. In addition, it is also excellent in the lipid-peroxidation-inhibitory effect due to the hydroxy radical-elimination effect and in the effect of improving the storage stability of, for instance, foods, beverages, cosmetics, pharmaceutical agents and feeds.

As causes of the skin-aging phenomena such as the formation of wrinkles and sags, there have been known the crosslinking of collagen, the reduction of the amount of collagen due to the reduction of a collagen-producing ability and the acceleration of a collagen-degrading ability and the fragmentation (conversion into low molecules) of inter-tissue substrate or mucopolysaccharides (mainly hyaluronic acid) and it has also been well known that active oxygen is involved in all of the foregoing phenomena. Among the active oxygen species serving as the causes thereof, hydroxyl radicals are the most reactive one and this greatly affects the formation of wrinkles and sags. In addition, superoxide has a relatively low reactivity, but may serve as a hydrogen peroxide source and accordingly, it may induce the formation of various other active oxygen species such as hydroxyl radicals. For this reason, it is an important active oxygen species involved in a variety of oxidative damages of, for instance, bio-components although the reactivity thereof is low.

As has been discussed above, a substance having such a hydroxyl radical-elimination activity would permit the inactivation of hydroxy radicals, which become a cause of the skin-aging phenomena and are the strongest active oxygen species. Moreover, a substance having a superoxide-elimination activity permits the inactivation of superoxide serving as a source of various other active oxygen species including hydroxy radicals and it would in turn permit the inhibition of the generation of any skin-aging-related substance and this results in the prevention of any aging.

Regarding the effect observed when the extract is used, the extract has a superoxide-elimination activity and a hydroxy radical-elimination activity in combination and the extract thus permits the inhibition of the generation of any substance serving as a cause of the skin-aging and the inactivation of the generated causative substance of the skin-aging. As a result, the extract may further contribute to the skin-aging inhibition.

When comparing the active oxygen-elimination function of the extract with those of other naturally occurring antioxidants, the superoxide-elimination activity of the extract derived from sesame lees, whose active oxygen-elimination function is considered to be relatively high, ranges from 5 to 10 unit/(mg/mL), while that of the extract of the present invention ranges from 20 to 65 unit/(mg/mL), which is quite high on the order of 2 to 13 times the superoxide-elimination activity of the extract derived from sesame lees.

Incidentally, the method of the present invention permits the preparation of an extract having a strong active oxygen-elimination function in a high yield per unit mass of the raw material. These facts indicate that the method permits the achievement of a very high level of the active oxygen-elimination function-yield index defined by the following <Formula 1> or the product of the intensity of the active oxygen-elimination function and the yield per unit mass of the raw material, as compared with the extracts derived from other natural raw materials. In other words, this means that the overall active oxygen-elimination function achieved per unit mass of the raw material is quite high. Thus, the preparation and use of the extract of the present invention would permit the production of a product having a strong active oxygen-elimination function and also permit the production of a large amount of a product when the extract of the invention is substituted for those derived from other natural raw materials since the overall active oxygen-elimination function achieved per unit mass of the raw material is quite high. Thus, the reduction of the production cost would likewise be expected. Accordingly, the present invention also relates to a method for preparing an extract, from olive plants, which permits the achievement of a high level of the overall active oxygen-elimination function-yield index per unit mass of the raw material. In this respect, favorable conditions for the production can be determined while taking into consideration this active oxygen-elimination function-yield index.

Active Oxygen-Elimination Function-Yield Index=(Intensity of Active Oxygen-Elimination Function)×(Yield per Unit Mass of Raw Material)(%)  <Formula 1>

Regarding the superoxide-elimination activity, the superoxide-elimination activity-yield index defined by the following <Formula 2> of the extract obtained per unit mass of the raw material ranges from about 100 to 3250. Therefore, the present invention likewise relates to a method for preparing an extract derived from olive plants having a superoxide-elimination activity-yield index per unit mass of the raw material of not less than 100. For instance, if comparing with the value for the extract derived from sesame, the extract of the present invention has a superoxide-elimination activity-yield index on the order of 1 to 650 times higher than that observed for the sesame extract since the index of the latter ranges from 5 to 100. In other words, the method of the present invention permits the preparation of a desired extract having a superoxide-elimination activity-yield index of 1 to 650 times while using the same amount of the raw material.

Superoxide-Elimination Activity-Yield Index=[Superoxide-Elimination Activity (unit/($mg/mL$))]×(Yield per Unit Mass of Raw Material)(%)   <Formula 2>

The extract of the invention has a strong melanin-production-inhibitory function. The term "melanin-production-inhibitory function" herein used means the function of inhibiting the biosynthesis of melanin pigment induced by the stimulation of melanocytes with the exposure thereof to ultraviolet rays, abnormal hormone metabolism thereof and genetic information. In general, it has been found that the melanocytes are stimulated by, for instance, the exposure thereof to ultraviolet rays and abnormal hormone metabolism to thus biosynthesis melanin pigment and the melanin pigment biosynthesized in the cells is deposited in the skin to thus cause dark skin, melasma, ephelis and dullness. Therefore, the occurrence of dark skin, melasma, ephelis and dullness may be eliminated or prevented by inhibiting the production of any melanin. In this respect, the extract of the present invention would show such a melanin-production-inhibitory function, the extract internally shows the effect when it is ingested, while the extract externally shows the effect when it is applied to, for instance, the skin and thus, the extract may contribute to, for instance, the maintenance of white and beautiful skin.

The extract of the present invention is evaluated using the melanin-production-inhibitory function defined below as an indication. The method comprises conducting a cultivation experiment using B-16 melanoma cells and evaluating the melanin-production-inhibitory function by comparing the cell-whitening degree (melanin-production-inhibitory function) with the cytotoxicity.

The B-16 melanoma cells possess a melanin-producing ability and the cells naturally grown or proliferated during the cultivation is pigmented black. If the culture system includes a substance capable of inhibiting the melanin-production during the proliferation, the darkening of the cells is suppressed, while the whitening thereof is promoted. Thus, the melanin-production-inhibitory function can be evaluated by comparing the degree of darkening of cells observed when any sample is not added with the degree of whitening of cells observed when the sample is added. In this connection, some of substances may be toxic to the B-16 melanoma cells. To evaluate this cytotoxicity, the cell-survival rate observed when a sample is not added is compared with that observed for the system free of any sample. The melanin-production-inhibitory function is evaluated using the cell-whitening degree and the cell-survival rate in combination.

An example of the method for inspecting a sample for the melanin-production-inhibitory function in a cell-cultivation system using B-16 melanoma cells comprising the steps of dispensing 2 ml/well of a culture medium to wells of 6-well plate, inoculating a desired amount of B-16 melanoma cells on each well, allowing the wells to stand at 37° C. and 5% $CO_2$, to thus cultivate the cells. On the day subsequent thereto, a sample (each of a variety of extracts derived from olive) solution prepared is added to the wells with stirring and the cultivation is then continued. The culture medium is replaced with fresh one on the $5^{th}$ day from the initiation of the cultivation and the sample solution is again added to the wells. On the next day, the culture medium is removed to recover the cells, followed by washing them with PBS (phosphate buffered physiological saline) and then evaluation of the cell-whitening degree. In this respect, the melanin-production-inhibitory function is evaluated by comparing the cell-whitening degree thus obtained with that observed when the same procedures used above are repeated except that 300 μg/ml of arbutin solution (positive control) is substituted for the sample solution used above and that observed when the same procedures used above are repeated except that any sample is not added (control).

The extract of the invention is a simple extract (untreated or crude extract), but has a melanin-production-inhibitory function identical or superior to those observed for arbutin and kojic acid, which have an excellent melanin-production-inhibitory function and are whitening agents having high whitening effects. Moreover, the extract has a quite strong melanin-production-inhibitory function substantially higher than those observed for vitamin C-magnesium phosphate. If the melanin-production-inhibitory function is expressed in terms of the melanin-production-inhibitory function index defined by the following <Formula 3>, while using arbutin as a control, a crude extract has a quite high melanin-production-inhibitory function index ranging from about 0.5 to 5 although it is a simple extract. Accordingly, the present invention also relates to an extract whose melanin-production-inhibitory function index is not less than 0.5. If the extract is further subjected to a concentration treatment and/or a fractionation-purification treatment, the quality of the extract is further improved and the melanin-production-inhibitory function index is likewise improved. For instance, the extract concentrated while making use of the solubility in water has a melanin-production-inhibitory function index improved to a level of about 8 to 20.

Melanin-Production-Inhibitory Function Index=$A/B$   <Formula 3> wherein A represents the concentration of positive control (arbutin 300 ppm) and B represent the concentration (ppm) of a test sample required for achieving the same whitening degree observed for the system to which the positive control (arbutin 300 ppm) is added.

The extract of the present invention has not only an excellent melanin-production-inhibitory function against B-16 melanoma cells, but also a quite low cytotoxicity to the B-16 melanoma cells and therefore, the toxicity thereof to the skin would be considered to be low.

For instance, if the cytotoxicity to B-16 melanoma cells is expressed in terms of the index of the toxicity to cells (cytotoxicity index) defined by the following <Formula 4> while using arbutin widely used as a whitening agent as a positive control, it is found that the extract of the invention has a low cytotoxicity index and therefore, it is less toxic to the skin as compared with arbutin.

Cytotoxicity Index=$C/D$   <Formula 4> wherein C represents the concentration of the positive control observed when the survival rate of B-16 melanoma cells is reduced to a level of not more than 10% (arbutin 500 ppm) and D represents the concentration of a test sample observed when the survival rate of B-16 melanoma cells is reduced to a level of not more than 10%.

In this respect, the term "cell-survival rate" herein used is defined by the following <Formula 5>:

Cell-Survival Rate(%)=$(E/F)\times 100$   <Formula 5>

E: Viable cell count observed for the system to which a sample is added.

F: Number of cells observed for the system free of any added test sample.

From the foregoing, the extract of the present invention has a toxicity to the skin lower than that observed for arbutin known as a whitening agent having an excellent melanin-production-inhibitory function and therefore, the former may be applied to the skin in a large amount. In other words, the extract may practically have a quite high whitening effect on the skin and the effect is higher than that achieved by arbutin as has been described above. In addition, this means that the extract can be incorporated into, for instance, cosmetics in a relatively high concentration and thus, the resulting cosmetics or the like containing the extract have considerably high whitening effect on the skin.

The amount of the extract capable of being practically applied to the skin and the overall intensity of the whitening effect thereof or the whitening effect expected when practically applying the extract to the skin can be expressed in terms of, as an indication, the substantial melanin-production-inhibitory function index defined by the following <Formula 6> on the basis of the melanin-production-inhibitory function and the toxicity to the skin observed for arbutin. If using the substantial melanin-production-inhibitory function index, the extract of the present invention has a quite high substantial melanin-production-inhibitory function index on the order of about 1 to 10 while arbutin is used as a control and therefore, the extract can practically exert a high whitening effect on the skin as compared with arbutin. Accordingly, the present invention also relates to an extract having an index of substantial whitening effect of not less than 1. The extract can further be subjected to concentration-purification to obtain a product having a high substantial melanin-production-inhibitory function index. For instance, an extract, which is concentrated while making use of the solubility in water, has a substantial melanin-production-inhibitory function index improved up to a level of about 8 to 20.

Substantial Melanin-Production-Inhibitory Function Index=(Melanin-Production-Inhibitory Function Index)/(Index of Toxicity to the Skin) <Formula 6>

In this respect, the preparation method of the present invention permits the preparation of an extract having a high melanin-production-inhibitory function and the achievement of a high yield per unit mass of the raw material. From these facts, it is found that the resulting extract has a considerably high melanin-production-inhibitory function-yield index and a considerably high substantial melanin-production-inhibitory function-yield index defined as a product of the intensity of the melanin-production-inhibitory function and the yield per unit mass of the raw material and expressed by the following <Formula 4> and <Formula 5> as compared with the extracts derived from other natural raw materials. In other words, this means that the method of the invention permits the achievement of a high overall melanin-production-inhibitory function per unit mass of the raw material. Accordingly, this means that the preparation and use of the extract of the present invention would permit the formation of a product having a strong skin-whitening effect and also permit the formation of a large amount of a product when the extract of the invention is substituted for other natural whitening agents since the overall melanin-production-inhibitory function and substantial melanin-production-inhibitory function achieved per unit mass of the raw material are quite high. Thus, the reduction of the production cost would likewise be expected.

Melanin-Production-Inhibitory Function-Yield Index=(Index of Melanin-Production-Inhibitory Function)×(Yield per Unit Mass of Raw Material)(%) <Formula 7>

Substantial Melanin-Production-Inhibitory Function-Yield Index= (Index of Substantial Melanin-Production-Inhibitory Function)× (Yield per Unit Mass of Raw Material)(%) <Formula 8>

When comparing the melanin-production-inhibitory function-yield index and substantial melanin-production-inhibitory function-yield index of the extract of the invention with those observed for other natural extracts, the melanin-production-inhibitory function index for the crude extract of the invention is high on the order of about 2 to 15 times that observed for, for instance, the water-soluble extract derived from sesame lees having a relatively high skin-whitening effect, while that observed for the extract, which is additionally subjected to concentration and/or fractionation-purification is quite high on the order of about 10 to 50 times that observed for the foregoing water-soluble extract. Moreover, the substantial melanin-production-inhibitory function index for the extract of the invention is on the order of about 2 to 15 times that observed for the water-soluble extract and the yield thereof is on the order of 1 to 10 times that observed for the water-soluble extract. Moreover, the melanin-production-inhibitory function-yield index thereof is on the order of 2 to 30 times that observed for the water-soluble extract and the substantial melanin-production-inhibitory function-yield index thereof is on the order of 2 to 40 times that observed for the water-soluble extract.

The extract of the invention has a skin melanin-production-inhibitory function and a yield higher than those observed for other natural whitening components and also has a melanin-production-inhibitory function index and a substantial melanin-production-inhibitory function index considerably higher than those observed for other natural whitening components. This means that the method of the present invention permits the achievement of a high overall intensity of the melanin-production-inhibitory function (melanin-production-inhibitory function-yield index and substantial melanin-production-inhibitory function-yield index) per unit mass of the raw material. Accordingly, this means that the preparation and use of the extract of the present invention would permit the production of a product having a strong skin-whitening effect and also permit the production of a large amount of a product when the extract of the invention is substituted for other natural whitening agents since the overall whitening effect achieved per unit mass of the raw material are quite high. Thus, the reduction of the production cost would likewise be expected.

Preferred conditions for preparing an extract can be determined using, as indications, the foregoing melanin-production-inhibitory function-yield index and substantial melanin-production-inhibitory function-yield index.

The extract of the invention has an active oxygen-elimination function and a melanin-production-inhibitory function. Examples of the active oxygen-elimination function include superoxide-elimination activity and hydroxyl radical-elimination activity. The extract also has an anti-aging effect for the skin, a skin-beautifying effect such as a whitening effect and an antioxidant effect, as secondary effects of the foregoing functions.

The external agent for the skin containing the extract of the invention having such functions shows an excellent anti-aging effect for the skin and a strong whitening effect. Thus, the external agent for the skin shows extremely excellent skin-beautifying effect.

The term "external agent for the skin" herein used includes pharmaceutical agents, quasi-drugs and cosmetics, which are applied to the skin and the dosage form thereof is not limited to any particular one. Examples of such dosage forms are cosmetics for skin care such as milky lotions, creams, toilet waters, packs and cleansings; cosmetics for make-up such as lip colors and foundations; cosmetics for the scalp; and pharmaceutical agents such as ointments, dispersions, creams and liquids for external use. The extract is derived from olive having good impression and therefore, it would impart psychological refreshing feeling and a sense of security to the consumers.

The olive plants as raw materials for the extract of the invention are stably available plant materials. The extract of the invention is prepared from a raw material or naturally occurring olive plants, which have widely been used as foods and/or edible materials and therefore, it is highly safe to the human body.

According to the present invention, an external agent for the skin containing an olive extract having a variety of functions can be prepared and in particular, the present invention permits the preparation of an external agent for the skin containing an extract having a skin-beautifying effect, in particular, an anti-aging effect for the skin and a whitening effect. Moreover, the present invention also permits the improvement of each function by subjecting the extract to a concentration treatment and/or a fractionation-purification treatment and the design of a proper combination of these effects by adjusting the intensity of each function. The present invention likewise permits the preparation of an external agent for the skin having an anti-aging effect for the skin of a desired intensity and a skin-beautifying effect such as a whitening effect, by appropriately controlling, for instance, conditions for the concentration of the extract.

The present invention relates to an external agent for the skin containing an extract prepared from olive plants, but the content of the extract may variously vary depending on the intended skin-beautifying effect such as anti-aging effect for the skin and a whitening effect, modes of application, the amount of the agent to be applied, and the degrees of the concentration and/or fractionation-purification and can appropriately be adjusted and thus is not restricted to any particular range. For instance, it is used in an amount ranging from 0.0001 to 50% by mass, preferably 0.0001 to 30% by mass, more preferably 0.01 to 30% by mass, particularly preferably 0.05 to 30% by mass, further preferably 0.1 to 30% by mass and most preferably 0.1 to 20% by mass.

In addition, the present invention relates to an external agent for the skin containing an extract obtained from olive plants as a skin-beautifying component and in particular, an external agent for the skin containing a skin-aging-inhibitory component and/or a whitening component. These agents have a skin-beautifying effect, in particular, an anti-aging effect for the skin and a whitening effect. The extract incorporated into the external agent for the skin may preferably be subjected to a concentration treatment and/or a fractionation-purification treatment and the effects of the extract can be controlled by appropriately adjusting the conditions for these treatments. Thus, these treatments can likewise control and/or design the effects of the resulting external agent for the skin of the present invention.

The term "skin-beautifying effect" herein used includes, for instance, an effect of eliminating or preventing the dark skin, melasma and ephelis generated or formed due to a variety of causes including, for instance, exposure to ultraviolet rays, changes in the hormone balance and genetic programs, an effect of lightening the dullness of the skin, an effect of making the skin transparent and beautiful or maintaining such transparent and beautiful skin, an effect of improving the gloss and/or tenseness of the skin, an effect of making the skin young and fresh or maintaining such young and fresh skin, and an effect of inhibiting or preventing the progress of the skin-aging phenomenon. In addition, the extract has an effect of inhibiting the generation of any odor such as body smells generated due to, for instance, the oxidative deterioration of sebaceous matter although this effect is not direct and/or visible effect and this is also considered to be a skin-beautifying effect in a broad sense. The external agent for the skin according to the present invention has all of the foregoing skin-beautifying effects due to the active oxygen-elimination function and the melanin-production-inhibitory function of the extract of the present invention, but it is, in particular, excellent in the whitening effect capable of eliminating or preventing the dark skin, melasma, ephelis and dullness and the anti-aging effect for the skin capable of inhibiting or preventing any progress of the skin-aging.

The term "anti-aging effect for the skin" herein used means the effect of eliminating and/or preventing any light-aging of the skin generated due to, for instance, exposure to ultraviolet rays and the aging of the skin along with the so-called aging due to any change in the hormone balance and/or any damage by the active oxygen. There has in general been known that active oxygen species generated by the exposure to ultraviolet rays and formed along with the life-maintaining actions of organisms, which are causative factors for forming wrinkles and sags, may damage the constituents of the skin such as lipids, saccharides and proteins. Therefore, if these active oxygen species can be eliminated, the foregoing wrinkles and sags or the skin-aging can be eliminated or prevented. In this respect, the external agent for the skin according to the present invention permits the restriction of any influence of these active oxygen species as low as possible since the extract included therein shows a superoxide-elimination activity and a hydroxy radical-elimination activity. Accordingly, the agent permits the elimination and prevention of any skin aging such as the formation of, for instance, wrinkles and sags and shows an excellent anti-aging effect for the skin.

The anti-aging effect for the skin can be evaluated by actually formulating a variety of agents externally applied to the skin such as creams, toilet waters and milky lotions and conducting sensory tests by female panelists using, for instance, the external agent for the skin. More specifically, a formulated external agent for the skin is applied to the skin of these panelists (15 women of 20-year-old to 50-year-old) twice a day in the morning and evening every day over several weeks. The anti-aging effect for the skin observed when the agent is actually applied can be evaluated by inspecting the panelists for the tenseness and gloss of the skin and the effect of relieving wrinkles and/or sags and then evaluating the sensory test results according to the following three criteria: effective; slightly effective; and not effective.

In the foregoing evaluation, the external agent for the skin or the like according to the present invention shows an anti-aging effect for the skin identical or superior to that observed for the extract derived from sesame lees as a control. More specifically, the external agent for the skin of the present invention has an excellent anti-aging effect for the skin.

The term "whitening effect" herein used means the effect of relieving or eliminating or preventing the dark skin, melasma, ephelis and dullness generated due to a variety of causative factors such as exposure to ultraviolet rays, change in the hormone balance and genetic programs. In general, it has been found that the melanocytes are stimulated by, for instance, the exposure thereof to ultraviolet rays and any change in the hormone balance, the melanin pigment biosynthesized in the cells is deposited in the skin to thus cause dark skin, melasma, ephelis and dullness. Therefore, the occurrence of dark skin, melasma, ephelis and dullness may be eliminated (or lightened) or prevented if the production of any melanin can be inhibited. In this respect, the external agent for the skin of the present invention comprises the extract of the invention and the latter has a melanin-production-inhibitory function and therefore, the former permits the production of such melanin pigment to a level as low as possible. For this reason, the agent of the invention permits the elimination or prevention of the foregoing dark skin, melasma, ephelis and dullness of the skin and thus shows an excellent whitening effect.

The whitening effect can likewise be evaluated by actually formulating a variety of agents externally applied to the skin such as creams, toilet waters and milky lotions and conducting sensory tests by female panelists using, for instance, the external agent for the skin. More specifically, a formulated external agent for the skin as a test sample is applied to the skin of these panelists (15 women of 20-year-old to 50-year-old) twice a day in the morning and evening every day over several weeks. The whitening effect observed when the agent is actually applied can be evaluated by inspecting the panelists for the effect of making the melasma, ephelis and dullness of the skin inconspicuous and then evaluating the sensory test results according to the following three criteria: effective; slightly effective; and not effective.

In the foregoing evaluation, the external agent for the skin or the like according to the present invention shows an anti-aging effect for the skin identical or superior to those observed for the extracts, as controls, to which arbutin and kojic acid as excellent whitening agents are incorporated. More specifically, the external agent for the skin of the present invention has an excellent whitening effect.

In this respect, the extract derived from the olive plants to be incorporated into the external agent for the skin may be a crude extract or extracts whose active oxygen-elimination function and melanin-production-inhibitory function are improved by subjecting a crude extract to a concentration and/or fractionation-purification treatments. Moreover, the extract may likewise be an extract whose active oxygen-elimination function or melanin-production-inhibitory function is improved or mixture thereof. The foregoing treatment such as concentration would permit the improvement of skin-beautifying effects such as skin-aging-inhibitory and whitening effects as secondary effects and therefore, these effects can be adjusted depending on each particular external agent for the skin having intended effects.

Moreover, embodiments of the external agent for the skin may include those comprising, in addition to the extract of the invention, at least one effective component selected from the group consisting of whitening agents, antioxidants, anti-inflammatory agents, cell activators, UV-screening agents, blood-circulation promoters and humectants.

As has been described above, other effective components may be incorporated into the external agent for the skin according to the present invention. In this case, it would be expected that the resulting agent show a synergistic effect of the extract of the invention and the added effective components. Specific examples of such effective components will be listed below.

The amount of the effective components incorporated into the external agent for the skin may vary depending on the kinds of the effective components selected, but it is preferred to use the same in an amount falling within the range specified below. The additional effective components never adversely affect the quality of the resulting product and can impart, for instance, higher whitening and skin-beautifying effects to the product inasmuch as the amount thereof falls within the range specified below.

Whitening agents other than those of the present invention include, for instance, vitamin C, derivatives thereof and salts thereof, arbutin, glutathione, placenta extracts, extracts of strawberry geranium, extracts of coix seeds, extracts of scutellaria roots, extracts from marine algae and wheat extracts.

Among these whitening agents, particularly preferred are vitamin C, derivatives thereof and salts thereof, arbutin, glutathione and placenta extracts.

The amount of the foregoing other whitening agents incorporated into the external agent for the skin according to the present invention preferably ranges from 0.00001 to 10% by mass and more preferably 0.0001 to 5% by mass on the basis of the total mass of the external agent for the skin of the invention. When using in combination with the whitening agent of the present invention, the ratio (by mass) of these whitening agents to the whitening agent of the invention preferably ranges from 0:100 to 95:5. When the placenta extract and plant extract are used in the liquid state, it is sufficient to use the same in such a manner that the dry solids content thereof falls within the range specified above. If the amount thereof falls within the range specified above, the resulting external agent for the skin has more excellent whitening and skin-beautifying effects and also provides good feeling when applied to the skin.

Examples of antioxidants usable herein include enzymes such as superoxide dismutase, catalase and glutathione peroxidase; tocopherol and derivatives thereof; dibutyl hydroxytoluene, butyl hydroxyanisole; carotenoids and derivatives thereof such as β-carotene; tannin and derivatives thereof such as gallic acid and ellagic acid; flavonoids such as flavone, catechin, quercetin and leucoanthocyanidin; quinones such as ubiquinone and vitamin K; thiamines and salts thereof; riboflavins such as riboflavin and riboflavin acetate; pyridoxines such as pyridoxine hydrochloride and pyridoxine dioctanoate; nicotinic acids such as nicotinic acid amide and benzyl nicotinate; bilirubin, mannitol, tryptophane, histidine, nordihydroguaiaretic acid.

Among these antioxidants, particularly preferred in the invention are superoxide dismutase, tocopherol and derivatives thereof, quercetin and mannitol.

The amount of these antioxidants to be incorporated into the external agent for the skin according to the present invention preferably ranges from 0.00001 to 5% by mass and more preferably 0.0001 to 3% by mass on the basis of the total mass of the external agent for the skin of the invention. In case where the plant extract is used in the liquid state without any post-treatment, it is sufficient to use the same in such a manner that the dry solids content thereof falls within the range specified above. If the amount thereof falls within the range specified above, the resulting external agent for the skin has a more excellent antioxidant effect, permits the prevention of any occurrence of inflammation, dark skin and skin-aging due to the formation of lipid peroxides within the skin and shows excellent whitening and skin-beautifying effects.

Examples of anti-inflammatory agents are glycyrrhizic acid, glycyrrhetic acid, allantoin, azulene, mefenamic acid, phenylbutazone, indometacin, ibuprofen, ketoprofen, ε-aminocaproic acid, hydrocortisone, panthenol and derivatives and salts thereof, zinc oxide, diclofenac sodium, aloe extract, extract of beefsteak plant, mugwort extract, camomile extract, comfrey extract, sanguisorba root extract and water-cress extract.

Particularly preferred anti-inflammatory agents are, for instance, glycyrrhizic acid, glycyrrhetic acid, derivatives thereof and salts thereof, among others.

The amount of the anti-inflammatory agent to be incorporated into the external agent for the skin of the present invention preferably ranges from 0.00001 to 5% by mass and more preferably 0.0001 to 3% by mass on the basis of the total mass of the external agent for the skin. In case where the plant extract is used in the liquid state without any post-treatment, it is sufficient to use the same in such a manner that the dry solids content thereof falls within the range specified above. If the amount thereof falls within the range specified above, the resulting external agent for the skin has an excellent anti-inflammatory effect and also shows excellent whitening and skin-beautifying effects.

As cell activators, there may be listed, for instance, royal jelly, photosensitizers, cholesterol and derivatives thereof, fetal calf blood extract, vitamin A and derivative thereof, citric acid, lactic acid, tartaric acid, malic acid, glycolic acid, succinic acid, serine, glutamic acid, hydroxyproline, theanine, pyrrolidone carboxylic acid, yeast extract, lactobacillus extract, *Bifidobacterium bifidum* extract and fermented metabolic extract.

Among these cell activators, particularly preferred are vitamin A and derivative thereof, citric acid, malic acid, lactic acid, serine and pyrrolidone carboxylic acid.

The amount of the cell activator to be incorporated into the external agent for the skin of the present invention preferably ranges from 0.00001 to 5% by mass and more preferably 0.0001 to 3% by mass on the basis of the total mass of the external agent for the skin. In case where the extract is used in the liquid state without any post-treatment, it is sufficient to use the same in such a manner that the dry solids content thereof falls within the range specified above. If the amount thereof falls within the range specified above, the resulting external agent for the skin has an excellent rough skin-curing effect and also shows excellent whitening and skin-beautifying effects.

Examples of UV-screening agents include benzoic acid type UV-screening agents such as p-aminobenzoic acid; anthranilic acid type UV-screening agents such as methyl ester of anthranilic acid, salicylic acid type UV-screening agents such as methyl salicylate, cinnamic acid type UV-screening agents such as methyl p-methoxy-cinnamate, benzophenone type UV-screening agents such as 2-hydroxy-4-methoxy-benzophenone, urocanic acid type UV-screening agents such as ethyl ester of urocanic acid, 4-t-butyl-4'-methoxybenzoyl methane, 2-(2'-hydroxy-5'-methylphenyl) benzotliazole, oxybenzene, titanium oxide, fine particulate titanium oxide and zinc oxide.

Particularly preferred UV-screening agents are, for instance, methyl p-methoxy-cinnamate, titanium oxide, fine particulate titanium oxide and zinc oxide, among others.

The amount of the UV-screening agent to be incorporated into the external agent for the skin of the present invention preferably ranges from 0.01 to 20% by mass and more preferably 0.1 to 10% by mass on the basis of the total mass of the external agent for the skin. If the amount thereof falls within the range specified above, the resulting external agent for the skin has an excellent UV-screening effect and also shows excellent whitening and skin-beautifying effects.

Examples of blood circulation promoters are swertia herb extract, cepharanthine, tocopherol and derivatives thereof, nicotinic acid and derivatives thereof, nonanoic acid vanillylamide, capsaicine, zingerone, cantharides tincture, ichthammol, caffeine, tannic acid, α-borneol, cyclandelate, cinnarizine, tolazoline, acetylcholine, verapamil, γ-oryzanol, camphor, hinokitiol, enzymes such as lipases and papain, red pepper extract, swertia herb extract, arnica extract, safflower extract and Japanese angelica root extract.

Among these blood circulation promoters, particularly preferred are, for instance, cepharanthine, tocopherol and derivatives thereof and γ-oryzanol.

The amount of the blood circulation promoter to be incorporated into the external agent for the skin of the present invention preferably ranges from 0.001 to 10% by mass and more preferably 0.01 to 20% by mass on the basis of the total mass of the external agent for the skin. If the amount thereof falls within the range specified above, the resulting external agent for the skin has an excellent blood circulation-promoting effect and also shows excellent whitening and skin-beautifying effects.

Examples of humectants are polyhydric alcohols such as glycerin, diglycerin, propylene glycol, dipropylene glycol, 1,3-butylene glycol and polyethylene glycol; proteins, derivatives thereof, hydrolyzates thereof and salts thereof such as collagen, elastin, keratin; amino acids and derivatives thereof such as glycine, aspartic acid and arginine; sorbitol, xylitol, erythritol, trehalose, inositol, glucose, sucrose and derivatives thereof; dextrin and derivatives thereof; sugars such as bees honey; D-panthenol and derivatives thereof; hyaluronic acid and salts thereof; mucopolysaccharides such as chondroitin sulfuric acid; pyrrolidone carboxylic acid salts, urea, phospholipids, glycolipids, ceramide and sodium lactate.

Examples of particularly preferred humectants are propylene glycol, proteins such as collagen, elastin and keratin, hyaluronic acid and salts thereof, and mucopolysaccharides such as chondroitin sulfuric acid.

The amount of the humectant to be incorporated into the external agent for the skin of the present invention preferably ranges from 0.001 to 70% by mass and more preferably 0.1 to 20% by mass on the basis of the total mass of the external agent for the skin. If the amount thereof falls within the range specified above, the resulting external agent for the skin has an excellent moisturizing effect and also shows excellent whitening and skin-beautifying effects.

These whitening agents, antioxidants, anti-inflammatory agents, cell activators, UV-screening agents, blood circulation promoters and humectants may be used alone or in any combination of at least two of them.

The external agent for the skin according to the present invention can be prepared by incorporating the extract into a base in a variety of forms or shapes, which have been known as the usual agents externally applied to the skin, according to the currently used method.

The shape of the formulated external agent for the skin is not restricted to any particular one and specific examples thereof include cosmetics, pharmaceutical agents for external use and quasi-drugs such as milky lotions, creams, toilet waters, packs, cosmetics for washing or cleansing, cosmetics for make-up, dispersions and ointments.

Moreover, the external agent for the skin according to the present invention may, if necessary, comprise other commonly used components in such an amount that the use thereof never adversely affects the effects of the present invention and specific examples thereof are water (purified water, hot spring water and deep-sea water), medicinal oils, surface active agents, metallic soap, gelatinizing agents, powders, alcohols, water-soluble polymers, film-forming agents, resins, clathrate compounds, antibacterial agents, perfumes, deodorants, salts, pH-controlling agents, refrigerants, extracts derived from plants, animals and microorganisms, astringents, lipid-leakage blocking agents, chelating agents, keratin-solubilizing agents, enzymes, hormones and vitamins. Specific examples of these components preferably used herein will be listed below. In this respect, the "derivative(s)" listed below includes salts capable of being prepared.

The medicinal oil is used herein for improving the handling ability of the constituents of the base and for improving the feeling upon use, may be any one inasmuch as it is used in the usual cosmetics and may be selected irrespective of, for instance, the origin and the quality thereof. Therefore, it may be a natural oil or a synthetic oil or may be in the form of a solid, a semisolid or a liquid. Examples thereof usable herein are hydrocarbons, waxes, fatty acids, higher alcohols, ester oils, silicone oils and fluorine atom-containing oils.

Specific examples of such medicinal oils are hydrocarbons such as squalane and vaseline; oils and fats derived from plants and animals such as olive oil, castor oil, jojoba oil, mink oil, macademia nuts oil, apricot oil, persic oil, safflower oil, sunflower oil, avocado oil, meduhome oil, camellia oil, almond oil, perilla oil, sesame oil, borage oil, cacao butter and shea butter; and waxes such as yellow bees wax, carnauba wax, candelilla wax and spermaceti.

The surfactant is used for emulsification or solubilization of, for instance, medicinal oil and examples thereof usable herein are anionic, cationic, nonionic and amphoteric surfactants.

The metallic soap may be, for instance, metal ions other than alkali metal salts of fatty acids and specific examples thereof are aluminum stearate, magnesium stearate and zinc laurate.

The gelatinizing agent is used for the stabilization of the resulting system, for improving the handling ability of the constituents of the base and for improving the feeling upon use and examples thereof include amino acid derivatives such as N-lauroyl-L-glutamic acid, dextrin fatty acid esters such as dextrin palmitic acid esters, sucrose esters of fatty acids, and clay minerals modified with organic substances.

The powder is mainly used for blocking a color or the skin in the cosmetics for make-up and for a wide variety of other purposes, for instance, for improving the feeling upon use and may be any powder inasmuch as it is commonly used in the usual cosmetics, irrespective of the shape (such as spherical, needle-like, plate-like shapes), particle size (fume, fine particles, pigment size) and/or particle structure (porous, nonporous). Specific examples thereof include inorganic powders such as barium sulfate, calcium carbonate, talc, mica, synthetic mica, mica, kaolin, sericite, silicic acid, silicic acid anhydride, aluminum magnesium silicate, ceramics powders and boron nitride; organic powders such as polyester powders, polyethylene powders, polystyrene powders, nylon powders and lauroyl lysine; colored pigments, for instance, inorganic pigments such as iron oxide, carbon black, chromium oxide, iron blue and ultramarine; lake pigment of tar-containing dye and lake pigment of natural dye; pearl pigments such as titanium oxide-coated mica, titanium oxide-coated mica, bismuth oxychloride, titanium oxide-coated bismuth oxychloride, titanium oxide-coated talc, fish scale flakes and titanium oxide-coated pigmented mica; other tar dyes; and naturally occurring dyes such as cochineal. These powders may be combined to form composites or may be surface-treated with medicinal oils, silicone or fluorine atom-containing compounds.

Examples of alcohols are lower alcohols such as ethanol and isopropanol; glycerin, diglycerin, ethylene glycol, diethylene glycol, triethylene glycol, propylene glycol, dipropylene glycol, 1,3-butylene glycol and polyethylene glycol.

The water-soluble polymer is used for improving the stability of the resulting system, the handling ability and the feeling upon use thereof or for imparting moisturizing effect to the system. Specific examples of water-soluble polymers are polymers derived from plants such as carrageenan, pectin, agar and locust bean gum; polymers derived from microorganisms such as xanthan gum; polymers derived from animals such as casein and gelatin; starch type polymers such as starch; cellulose type polymers such as methyl cellulose, ethyl cellulose, carboxymethyl cellulose, hydroxypropyl cellulose, nitrocellulose and crystalline cellulose; alginic acid type polymers such as sodium alginate; vinylic polymers such as carboxyvinyl polymer; polyoxyethylene type polymers; polyoxyethylene polyoxypropylene copolymer type polymers; acrylic polymers such as sodium polyacrylate; and inorganic water-soluble polymers such as bentonite and hectorite.

The water-soluble polymer also includes film-forming agents such as polyvinyl alcohol and polyvinyl pyrrolidone.

Examples of extracts derived from animals or microorganisms include fetal calf blood extract, protein free of serum, spleen, egg components derived from, for instance, fowls, chorion extract, cockscomb extract, shell extract, shellfish meat extract, royal jelly, silk protein and decomposition products thereof or derivatives thereof, hemoglobin and decomposition products thereof, lactoferrin or decomposition products thereof, mollusks such as cuttlefish ink, fish meat, extracts derived from animals such as mammals, fowls, shellfishes, insects, fishes, mollusks and crustaceans and extracts derived from microorganisms such as extract of *Fomes japonicus*. Various effects such as a moisturizing effect, a cell-activating effect, a whitening effect, an anti-inflammatory effect, an anti-aging effect for the skin, an active oxygen-elimination effect and a blood circulation-promoting effect can be imparted to the extract and/or the external agent for the skin by the addition of an extract derived from an animal or a microorganism thereto.

The extracts derived from plants are not limited in the sites to be extracted and methods for the extraction and may be those extracted from, for instance, roots, stems, trunks, barks, plumules, leaves, flowers, fruits and seeds. In this respect, the extraction can be conducted, for instance, by subjecting these raw materials to appropriate treatments such as drying, finely cutting, pressing or fermentation and then extracting these treated raw material with a variety of appropriate solvent at a low temperature or a temperature or under a gently heated conditions. Examples of extraction solvents are water; lower primary alcohols such as methyl alcohol and ethyl alcohol; liquid polyhydric alcohols such as glycerin, propylene glycol and 1,3-butylene glycol, which may be used alone or in any combination. It is also possible to conduct the extraction using a lipophilic solvent such as hexane, acetone, ethyl acetate and ether or the extract may likewise be one obtained by extracting with an oily component such as squalane. The resulting extract may further be subjected to absorption, discoloration and/or purification using filtration and/or an ion-exchange resin to thus convert the extract into, for instance, a solution, a paste, a gel or a powder. If necessary, the extract thus treated may further be subjected to a purification treatment such as deodorization and/or discoloration inasmuch as the treatments never adversely affect the effects of the extract. Examples of plants as sources for the extract are asparagus, rose fruits, raspberry, sophora roots, *Spatholobus suberectus* Dunn, acanthopanacis cortex, coffee, rice plant, asiasarum roots, crataegus, white lily, herbaceous peony, tea plant, Japanese beech, hops, Japanese dwarf quince, *Saxifraga stronifera* Meerburg, marshmallow, Angelica keiskei Koidz, Artemisia capillaries herba, nettle, phellodendron bark, *Hypericum erectum, lonicerae flos, Salvia officinalis*, lithospermum roots, white birch, *Sapindus mukurossi* Gaertn., Chinese milk vetch, barley, jujube, rosemary, coptis rhizome, grapefruit, gentian, *Saponaria officinalis L.*, Japanese iris, rehmannia roots, cnidium rhizome, tree mallow, witch-hazel (leaves), coltsfoots, Japanese (and Chinese) plum, *Tilia miqueliana*, horse-chestnut and *Cydonia oblonga* Mill. Various effects such as a moisturizing effect, a cell-activating effect, a whitening effect, an anti-inflammatory effect, an anti-aging effect for the skin, an active oxygen-elimination effect and a blood circulation-promoting effect can be imparted to the extract and/or the external agent for the skin by the addition of an extract derived from a plant.

Examples of antibacterial agents are benzoic acid, sodium benzoate, p-oxybenzoic acid esters, p-chloro-m-cresol, benzalkonium chloride, phenoxy ethanol and isopropyl methyl phenol.

In addition, the external agent for the skin of the invention may likewise comprise, if necessary, other currently used additives such as a preservative, a dye, a thickening agent, a perfume and/or a beautifying component.

Moreover, the external agent for the skin of the invention may be formed into pharmaceutical preparations together with, for instance, saccharides such as lactose and glucose; excipients such as dextrin, cellulose, silicates (salts) and calcium carbonate; binders such as cellulose, starch, gelatin and saccharides; and disintegrating agents such as agar powder, gelatin powder, sodium alginate, cellulose derivatives and calcium carbonate. Further, these preparations may be in any form such as liquids, solids, semisolids, emulsions and mousse.

The external agent for the skin of the present invention can be prepared according to the usual method and may have any form or dosage form such as a milky lotion, a cream, a toilet water, a beauty lotion, a cleansing, a pack, a cosmetic for washing or cleansing and a foundation, as well as other dispersions, granules and ointments.

In addition, the extract of the present invention is one suitably prepared from olive plants and therefore, it may optionally comprise other components originated from the olive plants. Examples of other components originated from the olive plants include triterpenes such as oleanolic acid and ursolic acid, sterols such as β-sitosterol and campesterol, and polyphenols such as Oleuropein, Verbascosid, Ligstrosid, tyrosol, hydroxytyrosol and rutin.

The foregoing components may, if necessary, be incorporated into the external agent for the skin of the invention to thus impart the effects of these components to the latter.

The present invention also relates to an oil-containing extract prepared from the fruits of olive plants. Moreover, the present invention likewise relates to an emulsified composition having a whitening effect, which is prepared by adding an emulsifying agent to the foregoing oil-containing extract.

The hardly water-soluble components of the extract of the invention may also be included in the olive oil and therefore, the use of the olive oil as a medicinal oil component of the external agent for the skin of the invention would permit the preparation of an external agent for the skin whose whitening effect or the like is further improved. Moreover, if the extract of the invention is prepared from seeds of olive plants containing oil components, the resulting oil-containing extract may comprise such oil components. In this regard, the oil-containing extract extracted from seeds containing oil components may be quite advantageous in that it can be used in an external agent for the skin, which requires the use of oil components. Moreover, an emulsifying agent may be added to the oil-containing extract to obtain an emulsified composition consisting of 100% olive and the emulsified composition may be incorporated into the external agent for the skin of the present invention. In particular, the external agent for the skin is used in the form of an emulsion in many cases and accordingly, this emulsified composition can be suitably incorporated into the external agent for the skin or may suitably be used as a base used for incorporating other substances into the agent.

Moreover, the emulsified composition is one derived from only the olive plants or a natural product and may give a feeling of security to the consumers. The olive has a favorable impression on the consumers and therefore, the emulsified composition completely derived from olive would give a good impression and a feeling of security to consumers and the use of the olive in such applications is quite preferred from the viewpoint of the effective use of the whole olive plant.

Examples of the foregoing emulsifying agents are non-ionic ones such as glycerin monostearate, polyoxyethylene (POE) sorbitan fatty acid esters, sorbitan fatty acid esters, POE alkyl ethers, POE·polyoxypropylene (POP) block copolymers and anionic ones such as fatty acid soap and sodium alkylsulfates.

Moreover, the present invention relates to a variety of pharmaceutical preparations comprising the extract of the invention as an effective component and in particular, to a skin-beautifying agent, a whitening agent and an anti-aging agent, which comprises the extract of the invention as an effective component.

In the skin-beautifying agent containing the extract of the invention, the "effective component" means that the agent comprises the extract in such an amount that the agent achieves the desired effect and the amount thereof is not particularly restricted. The amount of the effective component may appropriately be adjusted depending on, for instance, the intended degree of the skin-beautifying effect, the mode of applications, the amount of the agent, and the degrees of the concentration and/or fractionation-purification of the extract and is not particularly restricted as has been described above, but it is, for instance, not less than 0.001% by mass, preferably 0.01 to 99.9% by mass and more preferably 0.05 to 99.5% by mass. The extract can be prepared by extracting olive plants and/or products obtained during or after the olive oil-manufacturing process with water and/or an organic solvent and the resulting extract can further be subjected to concentration and/or fractionation-purification treatments to thus give a skin-beautifying agent whose effect is further improved. This skin-beautifying agent comprises both water-soluble and hardly water-soluble components and therefore, it may be used in both aqueous system and oil-based system after the removal of any insolubles. Alternatively, the skin-beautifying agent may, for instance, suitably be emulsified prior to use. Moreover, the skin-beautifying agent can be applied to the human body and used in other foods and beverages, pharmaceutical preparations, fertilizers, feeds and agents externally applied to the skin. It can be used internally through oral route and can be applied to, for instance, the skin. When the skin-beautifying agent is applied to the skin, it may directly be applied thereto for the purpose of beautifying the skin or may be used as a raw material for an external agent for the skin.

The present invention likewise relates to an anti-aging agent containing the foregoing extract having an anti-aging effect for the skin. Moreover, the present invention relates to cosmetics containing the foregoing extract and/or the foregoing anti-aging agent.

In the anti-aging agent comprising the extract as an effective component, the term "effective component" means, as has been described above, that the agent comprises the extract in such an amount that the agent achieves the desired effect and the amount thereof is not particularly restricted. The amount of the effective component may appropriately be adjusted depending on, for instance, the intended degree of the anti-aging effect for the skin, the mode of applications, the amount of the agent, and the degrees of the concentration and/or fractionation-purification of the extract and is not particularly restricted as has been described above, but it is, for instance, not less than 0.01% by mass, preferably not less than 0.1% by mass, more preferably 0.1 to 99.9% by mass, further preferably 0.5 to 99.5% by mass, particularly preferably 1 to 95% by mass and most preferably 2 to 90% by mass. The extract can be prepared by extracting olive plants and/or products obtained during or after the olive oil-manufacturing process with water and/or an organic solvent and the resulting extract can further be subjected to concentration and/or fractionation-purification treatments to thus give an anti-aging agent whose effect is further improved. The anti-aging agent is water-soluble and therefore, it is suitably applied to aqueous systems among others. Alternatively, it may be applied to oil systems after, for instance, the emulsification thereof. Moreover, the anti-aging agent can be applied to the human body and used in other foods and beverages, pharmaceutical preparations, fertilizers, feeds and agents externally applied to the skin. It can be used internally through oral route and can be applied to, for instance, the skin. When the anti-aging agent is applied to the skin, it may directly be applied thereto for the purpose of enjoying the anti-aging effect for the skin or may be used as a raw material for an external agent for the skin.

The present invention likewise relates to a whitening agent containing the foregoing extract having a whitening effect, as an effective component. The present invention further relates to a whitening agent containing the foregoing extract having a whitening effect and/or the foregoing whitening agent.

The term "effective component" means, as has been described above, that the agent comprises the extract in such an amount that the agent achieves the desired effect and the amount thereof is not particularly restricted. The amount of the effective component may appropriately be adjusted depending on, for instance, the intended degree of the whitening effect, the mode of applications, the amount of the agent, and the degrees of the concentration and/or fractionation-purification of the extract and is not particularly restricted as has been described above, but it is, for instance, not less than 0.001% by mass, preferably 0.01 to 99.9% by mass, more preferably 0.05 to 99.5% by mass, particularly preferably not less than 0.5% by mass, further preferably 1 to 95% by mass and most preferably 2 to 90% by mass. The extract can be prepared by extracting olive plants and/or products obtained during or after the olive oil-manufacturing process with water and/or an organic solvent and the resulting extract can further be subjected to concentration and/or fractionation-purification treatments to thus give a skin-beautifying agent whose effect is further improved. The whitening agent is hardly water-soluble and therefore, it is preferably applied to oil-based systems among others. Alternatively, it may be applied to aqueous systems after, for instance, the emulsification thereof. Moreover, the whitening agent can be applied to the human body and used in other foods and beverages, pharmaceutical preparations, fertilizers, feeds and agents externally applied to the skin. It can be used internally through oral route and can be applied to, for instance, the skin. When the skin-beautifying agent is applied to the skin, it may directly be applied thereto for the purpose of beautifying the skin or may be used as a raw material for an external agent for the skin.

The foregoing skin-beautifying agent can be formed into a pharmaceutical preparation according to the usual method, but the extract used therein as an effective component may be either a crude extract or one subjected to concentration and/or fractionation-purification treatments. Regarding the anti-aging effect for the skin and the whitening effect of the skin-beautifying agent, the skin-beautifying agent containing, for instance, the water-soluble fraction of the extract has a higher anti-aging effect for the skin, while the skin-beautifying agent containing, for instance, the hardly water-soluble fraction of the extract has a higher whitening effect. For this reason, it is often preferred to use an extract obtained by concentrating and/or fractionating-purifying the water-soluble component and/or the hardly water-soluble component depending on the intended skin-beautifying effect.

The foregoing anti-aging agent can likewise be formed into a pharmaceutical preparation according to the usual method, but the extract used therein as an effective component may be either a crude extract or one subjected to concentration and/or fractionation-purification treatments and in particular, it is preferred to use an extract prepared by concentrating and/or fractionating-purifying the water-soluble component. Regarding the effect of the extract, the inhibitory agent containing, for instance, the water-soluble fraction has a higher anti-aging effect for the skin and therefore, it is preferred, in this case, to use the extract obtained by, for instance, concentrating the water-soluble component.

The foregoing whitening agent can also be formed into a pharmaceutical preparation according to the usual method, but the extract used therein as an effective component may be either a crude extract or one subjected to concentration and/or fractionation-purification treatments and in particular, it is preferred to use an extract prepared by concentrating and/or fractionating-purifying the hardly water-soluble component. Regarding the effect of the extract, the whitening agent containing, for instance, the hardly water-soluble fraction has a higher whitening effect and therefore, it is preferred, in this case, to use the extract obtained by, for instance, concentrating the hardly water-soluble component.

The external agent for the skin according to the present invention may be used in a variety of forms, for instance, solids such as powder obtained by drying the same; liquids such as those prepared by diluting the extract with water or a solvent; and emulsions and gels, but may likewise be formed into pharmaceutical preparations such as powders, capsules (such as hard capsules and soft capsules), granules (coated granules, pills, troches, liquid preparations, or pharmaceutically acceptable sustained release preparations thereof).

These pharmaceutical preparations may be combined with pharmaceutically acceptable additives such as bases, carriers, excipients, disintegrators, lubricants and coloring agents according to the known pharmaceutical preparation method.

Examples of carriers and excipients used in these pharmaceutical preparations are lactose, glucose, sucrose, mannitol, potato starch, corn starch, calcium carbonate, calcium phosphate, calcium sulfate, crystalline cellulose, powdered glycyrrhiza, and powdered gentian.

Examples of binders used in these pharmaceutical preparations include starch, tragacanth gum, gelatin, syrup, polyvinyl alcohol, polyvinyl ether, polyvinyl pyrrolidone, hydroxypropyl cellulose, methyl cellulose, ethyl cellulose and carboxymethyl cellulose.

Examples of disintegrators used in these pharmaceutical preparations include starch, agar, powdered gelatin, sodium carboxymethyl cellulose, calcium carboxymethyl cellulose, crystalline cellulose, calcium carbonate, sodium hydrogen carbonate and sodium alginate.

Examples of lubricants used in these pharmaceutical preparations include magnesium stearate, talc, hydrogenated vegetable oils and macrogol.

The coloring agents used in these pharmaceutical preparations may be those commonly pharmaceutically acceptable.

When preparing a tablet or a granule, it may be coated with sucrose, gelatin, hydroxypropyl cellulose, purified shellac, gelatin, glycerin, sorbitol, ethyl cellulose, hydroxypropyl cellulose, hydroxypropyl methyl cellulose, polyvinyl pyrrolidone, cellulose phthalate acetate, hydroxypropyl methyl cellulose phthalate, methyl methacrylate and methacrylic acid polymer, which may be used alone or in any combination of at least two of them. Alternatively, it may be encapsulated in a capsule of, for instance, ethyl cellulose or gelatin.

When the pharmaceutical preparation is applied to the skin, it may be in a solid, semisolid, semisolid-like or liquid-like state.

Examples of liquid pharmaceutical preparations are pharmaceutically acceptable emulsions such as emulsions or lotions and tinctures externally applied to the skin. This pharmaceutical preparation may comprise a commonly used diluent such as ethanol, an oil fraction and an emulsifying agent.

Examples of such semisolid pharmaceutical preparations are ointments such as an oil-based ointment and a hydrophilic ointment. This pharmaceutical preparation comprises, for instance, water, vaseline, polyethylene glycol, an oil fraction and/or a surfactant as a commonly used base or a carrier.

Examples of semisolid or solid pharmaceutical preparations are a hard plaster (such as rubber plaster and plaster), films, tapes, cataplasms, packs and bath medicines. These pharmaceutical preparations may comprise, as a currently used base or carrier, a rubber type polymer such as natural rubber, and a synthetic rubber such as butadiene rubber, SBR or SIS; a suspending agent such as gelatin, kaolin and zinc oxide; a hydrophilic polymer such as sodium carboxymethyl cellulose and sodium polyacrylate; a tackifier such as an acrylic resin and liquid paraffin; water, other oil fraction and/or a surfactant.

These pharmaceutical preparations may likewise comprise an auxiliary agent such as a stabilizer, a solubilizing agent and a percutaneous absorption-promoter; or an additive such as an aromatic and a preservative.

The present invention relates to an external agent for the skin containing the foregoing skin-beautifying agent. The use the skin-beautifying agent would permit the preparation of an external agent for the skin having a skin-beautifying effect. The amount of the skin-beautifying agent to be incorporated into the agent externally applied may appropriately be controlled while taking into consideration the degree of the desired effect of the intended agent externally applied, the modes of applications thereof, the amount of the agent externally applied and the intensity of the skin-beautifying agent. For instance, the amount thereof ranges from 0.0001 to 50% by mass, preferably 0.0001 to 40% by mass and more preferably 0.0001 to 30% by mass, but the amount is not restricted to the range specified above at all. Moreover, the amount of the skin-beautifying agent to be incorporated into the external agent for the skin, for instance, ranges from 0.0001 to 30% by mass, preferably 0.0001 to 20% by mass and more preferably 0.0001 to 10% by mass on the basis of the total amount of the extract.

Moreover, the present invention relates to an external agent for the skin containing the foregoing anti-aging agent and/or the foregoing whitening agent. The use of the skin-beautifying agent, the anti-aging agent and the whitening agent would permit the preparation of an external agent for the skin having an anti-aging effect for the skin and a whitening effect. The amount of these anti-aging agent and whitening agent to be incorporated into the agent externally applied may appropriately be controlled while taking into consideration the degree of the desired effect of the intended agent externally applied, the modes of applications thereof, the amount of the agent externally applied and the intensities of the anti-aging agent and the whitening agent. For instance, the amount thereof ranges from 0.0001 to 50% by mass, preferably 0.0001 to 40% by mass and more preferably 0.0001 to 30% by mass, but the amount is not restricted to the range specified above at all. Moreover, the amount of the anti-aging agent and the whitening agent to be incorporated into the external agent for the skin, for instance, ranges from 0.0001 to 30% by mass, preferably 0.0001 to 20% by mass and more preferably 0.0001 to 10% by mass on the basis of the total amount of the extract.

The intended strength of the whitening effect of the extract having such whitening effect can appropriately be adjusted depending on the kind of the subject to which the extract is added. The amounts of the extracts to be incorporated into the external agent for the skin such as cosmetics is not indiscriminately determined because of the difference in raw materials and the difference in the content of the water-soluble components. However, when the extract of the present invention is incorporated into the external agent for the skin, the amount thereof, for instance, ranges from 0.05 to 30% by mass, preferably 0.1 to 20% by mass and more preferably 0.3 to 10% by mass. For this reason, the external agent for the skin such as cosmetics is considered to be safe for the human body, excellent in the storage stability and excellent in the skin-whitening effect.

Moreover, the extract and/or aging-inhibitory agent according to the present invention may favorably be incorporated into agents externally applied to the skin such as cosmetics, quasi-drugs, and pharmaceutical agents. In this respect, the content of the extract of the invention in the external agent for the skin can appropriately be controlled depending on the intended intensity of the anti-aging effect for the skin and the subject to which the extract is to be added. The content thereof ranges from 0.01 to 50% by mass, preferably 0.05 to 30% by mass and more preferably 0.1 to 30% by mass, although the content or amount of the extract is not limited to the range specified above. For this reason, the external agent for the skin such as cosmetics is considered to be safe for the human body, excellent in the storage stability and excellent in the anti-aging effect for the skin.

Thus, the use of the external agent for the skin according to the present invention would permit the achievement of a skin-beautifying effect due to the anti-aging effect for the skin and the whitening effect of the extract or an excellent anti-aging effect for the skin such as the improvement of the tenseness and gloss of the skin and the prevention of any formation of wrinkles and/or sags as well as an excellent skin-beautifying effect due to the whitening effect such as the elimination or prevention of any occurrence of dark skin, melasma, ephelis and dullness.

Furthermore, the extract of the present invention may easily be prepared from olive plants or may suitably be prepared from the products formed during or after the olive oil-manufacturing process and commonly discarded and therefore, the present invention is quite favorable from the viewpoint of the production cost, the stable supply, and the effective use of the natural resource.

EXAMPLES

Then the present invention will hereunder be described in more detail with reference to the following Examples, but the present invention is not restricted to these specific Examples at all.

A variety of extracts were prepared in the following Examples 1 to 19 and Comparative Example 1. The yields appearing in the following Examples were determined according to the following relation: <Formula 9>:

Yield of Extract=(Mass of Extract (Note 1))/(Mass of Raw Material Before Extraction (Note 2))      <Formula 9>

Note 1: The mass (g) was determined after drying by freeze-drying.
Note 2: The mass (g) of fruits, seedcake and seeds was determined immediately before initiating the extraction for preparing the extract.

Example 1

Dried fruits (including seeds) (1 kg) of native olive (*Olea europaea* L.) were crushed and 3 L of hexane was added to the crushed dried fruits to conduct the extraction thereof for 3 hours. The foregoing operations were repeated 4 times to obtain defatted fruits, the seeds were removed from the fruits, the fruits thus treated were pulverized and the fruits were again extracted with 5 volumes of hexane for 3 hours to give 229 g of defatted lees from which the oil components were completely removed. To the defatted lees, there was added 10 volumes of water-containing ethanol having an ethanol content of 60% by mass, followed by extraction at room temperature for 3 hours with vigorous stirring. The whole of the extraction system was filtered and the resulting filtrate was concentrated to dryness to give 112.7 g of an extract.

The resulting extract was inspected for the superoxide-elimination activity and the hydroxy radical-elimination activity. The results thus obtained are listed in the following Tables 1 and 2. The resulting extract was also inspected for the melanin-production-inhibitory function and the rate of cell survival. The results obtained are listed in the following Table 3. Further, the following Table 4 shows the yield, melanin-production-inhibitory function index, substantial melanin-production-inhibitory function index, melanin-production-inhibitory function-yield index and substantial melanin-production-inhibitory function-yield index of the extract.

Example 2

The same procedures used in Example 1 were repeated to obtain defatted lees. Then 10 volumes of a water-containing ethanol solution having an ethanol content of 80% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 79.7 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 3

The same procedures used in Example 1 were repeated to obtain defatted lees. Then 10 volumes of a water-containing ethanol solution having an ethanol content of 70% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 97.8 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 4

The same procedures used in Example 1 were repeated to obtain defatted lees. Then 10 volumes of a water-containing ethanol solution having an ethanol content of 50% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 111.1 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index are summarized in the following Table 4.

Example 5

The same procedures used in Example 1 were repeated to obtain defatted lees. Then 10 volumes of a water-containing ethanol solution having an ethanol content of 40% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 112.9 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 6

The same procedures used in Example 1 were repeated to obtain defatted lees. Then 10 volumes of a water-containing ethanol solution having an ethanol content of 20% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 110.6 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 7

The same procedures used in Example 1 were repeated to obtain defatted lees. Then 10 volumes of anhydrous ethanol were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 13.5 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 8

The same procedures used in Example 1 were repeated to obtain defatted lees. Then 10 volumes of water were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 118.2 g of an extract.

The resulting extract was inspected for the superoxide-elimination activity. The result thus obtained is listed in the following Table 1.

Example 9

The same procedures used in Example 1 were repeated to obtain defatted lees. Then 10 volumes of water-containing acetone having an acetone content of 60% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 51.5 g of an extract.

The resulting extract was inspected for the superoxide-elimination activity. The result thus obtained is listed in the following Table 1.

Example 10

The same procedures used in Example 1 were repeated to obtain defatted lees. Then 10 volumes of water-containing THF having a THF content of 60% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 54.3 g of an extract.

The resulting extract was inspected for the superoxide-elimination activity. The result thus obtained is listed in the following Table 1.

Example 11

The same procedures used in Example 1 were repeated to obtain defatted lees. Then 10 volumes of water-containing AN having an AN content of 60% by mass were added to the defatted lees and the extraction of the defatted lees was conducted at room temperature for 3 hours with vigorous stirring in the same manner used in Example 1. The whole of the extraction system was filtered and the resulting filtrate was concentrated to dryness to give 54.3 g of an extract.

The resulting extract was inspected for the superoxide-elimination activity. The result thus obtained is listed in the following Table 1.

Example 12

Dried fruits of olive (1 kg) from which seeds had been removed were crushed, 20 volumes of a water-containing ethanol solution having an ethanol content of 60% by mass were added to the crushed dried fruits and the extraction of the fruits was conducted at room temperature for 3 hours with vigorous stirring in the same manner used above. The whole extraction system was filtered, the resulting filtrate was concentrated to dryness to give 238.5 g of an extract. To the resulting extract, there were added 1.5 L of hexane and 1.5 L of water, followed by sufficient stirring, concentration of the resulting aqueous phase thus separated to dryness to give 126.4 g of a fractionated extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 13

Seeds of olive (500 g) were crushed, 10 volumes of a water-containing ethanol solution having an ethanol content of 60% by mass were added to the crushed olive seeds and the extraction thereof was conducted at room temperature for 3 hours with vigorous stirring in the same manner used above. The whole extraction system was filtered and the resulting filtrate was concentrated to dryness to give 42.0 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 14

Olive plants (*Olea europaea L.*) indigenous to Italy were subjected to oil expression, 3 L of hexane was added to 1 kg of the resulting pressed cake and the extraction thereof was conducted for 3 hours. The extraction procedures were repeated 4 times and then the seeds and foreign matter were removed from the resulting defatted residue (884 g) through filtration to give 196 g of defatted lees. To the defatted lees, there were added 10 volumes of a water-containing ethanol solution having an ethanol content of 60% by mass and the extraction thereof was conducted at room temperature for 3 hours with vigorous stirring. The whole extraction system was filtered and the resulting filtrate was concentrated to dryness to give 19.2 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 15

To the defatted lees prepared according to the same procedures used in Example 14, there were added 10 volumes of a water-containing ethanol solution having an ethanol content of 70% by mass and the extraction thereof was conducted at room temperature for 3 hours with vigorous stirring. The whole extraction system was filtered and the resulting filtrate was concentrated to dryness to give 17.4 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 16

Olive plants (*Olea europaea L.*) indigenous to Italy were subjected to oil expression, 3 L of hexane was added to 1 kg of the resulting pressed cake and the extraction thereof was conducted for 3 hours. The extraction procedures were repeated 4 times and then the resulting defatted residue (884 g) was pulverized without removing the seeds or the like to give 873 g of pulverized, defatted lees. To the pulverized, defatted lees, there were added 10 volumes of a water-containing ethanol solution having an ethanol content of 60% by mass and the extraction thereof was conducted at room temperature for 3 hours with vigorous stirring. The whole extraction system was filtered and the resulting filtrate was concentrated to dryness to give 39.5 g of an extract.

The resulting extract was inspected for the superoxide-elimination activity. The result thus obtained is listed in the following Table 1. Moreover, the results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 17

To the pulverized, defatted lees prepared according to the same procedures used in Example 16, there were added 10 volumes of a water-containing ethanol solution having an ethanol content of 60% by mass and the extraction thereof was conducted for 3 hours with vigorous stirring. The whole extraction system was filtered, the ethanol was completely removed from the resulting filtrate to give the aqueous fraction of the extract, water was added thereto in such an amount that the total amount of the system was 830 g for the purpose of improving the recovery efficiency of the water-insoluble fraction and then the resulting mixture was vigorously stirred at room temperature for one hour. The whole mixture was centrifuged to remove the precipitates and then the resulting supernatant was recovered by decantation, followed by drying and concentration of the supernatant to give 22.9 g of a concentrate.

The extract obtained after the concentration was inspected for the superoxide-elimination activity. The result thus obtained is listed in the following Table 1.

Example 18

To 100 g of the extract prepared in Example 1, there was added 2 L of water and then the resulting mixture was vigorously stirred at room temperature for one hour. The whole mixture was centrifuged, the resulting supernatant was removed by decantation and the remaining precipitates were dried to give 10.0 g of an extracted concentrate.

The results of the inspection of the resulting extract obtained after the concentration for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Example 19

To 100 g of the extract prepared in Example 14, there was added 2 L of water and then the resulting mixture was vigorously stirred at room temperature for one hour. The whole mixture was centrifuged, the resulting supernatant was removed through decantation and the remaining precipitates were dried to give 42.0 g of an extracted concentrate.

The results of the inspection of the resulting extract obtained after the concentration for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

Comparative Example 1

Dried sesame seeds (1 kg) were crushed, followed by addition of 3 L of hexane and extraction for 3 hours. These procedures were repeated 4 times to give 526.4 g of defatted lees of sesame. To the resulting defatted lees of sesame, there were added 10 volumes of a water-containing ethanol solution having an ethanol content of 60% by mass and the extraction thereof was conducted at room temperature for 3 hours with vigorous stirring. The whole extraction system was filtered and the resulting filtrate was concentrated to dryness to give 58.2 g of an extract.

The extract prepared from sesame seeds was inspected for the superoxide-elimination activity and the hydroxy radical-elimination activity. The results thus obtained are listed in the following Tables 1 and 2. The results of the inspection of the resulting extract for the melanin-production-inhibitory function (degree of cell-whitening and rate of cell survival) are listed in the following Table 3. Further, the yield, melanin-production-inhibitory function index, substantial melanin-production-inhibitory function index, melanin-production-inhibitory function-yield index and substantial melanin-production-inhibitory function-yield index of the extract are summarized in the following Table 4.

BHA (Comparative Example 2), which was a synthetic antioxidant having a superoxide-elimination activity was inspected for the superoxide-elimination activity. The result thus obtained is listed in the following Table 1.

Vitamin C-magnesium phosphate (Comparative Example 3) and kojic acid (Comparative Example 4) were inspected for the melanin-production-inhibitory functions. The results thus obtained are summarized in the following Table 3. Further, the melanin-production-inhibitory indexes and the substantial melanin-production-inhibitory indexes of these substances are listed in the following Table 4.

The following are methods for evaluating active oxygen-elimination and melanin-production-inhibitory functions and the results of such evaluation. The active oxygen-elimination function is evaluated by the determination of superoxide-elimination and hydroxy radical-elimination activities, whose evaluation methods and evaluated results are detailed below.

<Method for the Evaluation of Superoxide-Elimination Activity>

The evaluation of the superoxide-elimination activity was determined as follows, according to the method disclosed in "Experimental Methods of Lipid Peroxides", edited by KANEDA Yasushi & UEDA Nobuo, pp. 136–154, ISHIYAKU Publishing Company, 1993. To 1.2 mL of sodium hydrogen carbonate buffer (pH 10.2), there were added 50 $\mu$L of a 1 mg/mL EDTA solution, 50 $\mu$L of a 1.5 mg/mL bovine serum albumin (BSA), 50 $\mu$L of a 0.6 mg/mL nitroblue tetrazolium (NBT) solution, 50 $\mu$L of a 0.5 mg/mL xanthine solution and 0.1 mL of a "sample solution" obtained by dissolving an olive extract in a predetermined concentration, followed by admixing them and allowing it to stand at 25° C. for 10 minutes. To the resulting mixture, there was added 50 $\mu$L of a 0.1 unit/mL xanthine oxidase (XOD) solution, followed by stirring the mixture and allowing it to stand at 25° C. for 20 minutes. After 50 $\mu$L of a 1 mg/mL copper chloride solution was added to the resulting mixture to stop the enzyme reaction, the absorbance (G) at 560 nm was determined. Separately, a control solution was prepared by repeating the same procedures used above except for using the same amount of the "buffer" instead of the "sample solution" and the absorbance (H) thereof was likewise determined. In addition, sample blanks were prepared by reversing the order of addition of the copper chloride solution and the "sample solution" or the "buffer", respectively and the absorbance values of these blanks were likewise determined, which were hereunder referred to as g and h, respectively.

On the other hand, butyl hydroxyanisole (BHA) as a commercially available antioxidant was used as a comparative antioxidant. The absorbance value (G) of BHA was determined by the same method used above except for the following points. More specifically, the sodium carbonate buffer (pH 10.2) was added in an amount of 1.25 mL, a "BHA solution" prepared by dissolving it in methanol in a desired concentration was added in an amount of 50 $\mu$L and an XOD solution having a concentration of 0.2 unit/mL was prepared and used. Further, a control solution was prepared by substituting the same amount of "methanol" for the "BHA solution" and used for the determination of the absorbance value (H). In addition, sample blanks were prepared by reversing the order of addition of the copper chloride solution and the "BHA solution" or the "methanol", respectively and the absorbance values of these blanks were likewise determined, which were hereunder referred to as g and h, respectively.

Then each superoxide-elimination activity was calculated according to the following relation: <Formula 10>. In this connection, "I" appearing in this formula represents the sample concentration in the test solution system and the activity required for eliminating superoxide to thus reduce the absorbance value by 0.1 is defined to be one unit (1 unit). It should recognized that the higher the activity value, the stronger the superoxide-elimination action.

Superoxide-Elimination Activity (unit/($mg/mL$))=[($H-h$)−($G-g$)]/($I$×0.1)  <Formula 10>

TABLE 1

| Ex. No. | Raw Material | Extract | Yield (%) | SOE Act.[1] | SEA-Y Index[2] |
|---|---|---|---|---|---|
| 1 | Defatted Lees 1 | 60%: H₂O—EtOH | 49.2 | 60 | 2952 |
| 2 | Defatted Lees 1 | 80%: H₂O—EtOH | 34.8 | 31.2 | 1087 |
| 3 | Defatted Lees 1 | 70%: H₂O—EtOH | 42.7 | 68 | 2904 |
| 4 | Defatted Lees 1 | 50%: H₂O—EtOH | 48.5 | 58 | 2813 |
| 5 | Defatted Lees 1 | 40%: H₂O—EtOH | 49.3 | 56.3 | 2775 |
| 6 | Defatted Lees 1 | 20%: H₂O—EtOH | 48.3 | 33.6 | 1623 |
| 7 | Defatted Lees 1 | 100%: Anhydrous EtOH | 5.9 | 25.9 | 153 |
| 8 | Defatted Lees 1 | Water | 51.6 | 24.8 | 1281 |
| 9 | Defatted Lees 1 | 60%: H₂O-Acetone | 22.5 | 17.1 | 385 |
| 10 | Defatted Lees 1 | 60%: H₂O—THF | 23.7 | 18.9 | 448 |
| 11 | DefattedLees 1 | 60%: H₂O—AN | 21.7 | 14.1 | 306 |
| 12 | Dried Fruit Free of Seeds | 60%: H₂O—EtOH | 12.6 | 42.4 | 534 |
| 13 | Defatted Seeds Ground Product | 60%: H₂O—EtOH | 8.4 | 25.4 | 213 |
| 14 | Defatted Lees 2 | 60%: H₂O—EtOH | 9.8 | 23.4 | 229 |
| 15 | Defatted Lees 2 | 70%: H₂O—EtOH | 8.9 | 29.5 | 263 |
| 16 | Defatted Lees 3 | 60%: H₂O—EtOH | 4.5 | 22.8 | 103 |
| 17 | Concentrate of Ex. 16 | Recovered Water-Soluble Fraction | 2.6 | 39.5 | 103 |
| 1* | Sesame defatted Lees | 60%: H₂O—EtOH | 11.1 | 7 | 77 |
| 2* | BHA | | | 25 | — |

"%" appearing in the column entitled "Extract" represents the content of solvent in terms of "% by mass".
Defatted Lees 1: This is prepared by removing seeds from dried fruits of native olive and then subjecting them to the removal of fats.
Defatted Lees 2: This is prepared by removing seeds from pressed residue of olive native of Italy and then subjecting it to the removal of fats.
Defatted Lees 3: This is prepared by subjecting pressed residue of olive native of Italy to the removal of fats (including seeds).
[1]Superoxide-elimination activity [unit/(mg/mL)]
[2]Superoxide-elimination activity-yield index.
*Comparative Example The data listed in Table 1 indicate that the extract of the present invention has a considerably strong superoxide-elimination activity. In particular, when the extraction is conducted using water, anhydrous alcohol and water-containing alcohol, the extract of the invention shows an elimination activity on the order of about 1 to 2 times that achieved by BHA as a typical synthetic antioxidant, although the extract is a natural one. It is found that even an extract immediately after the extraction (sample or crude extract) has a very strong superoxide-elimination activity.

Furthermore, the extract of the invention can be prepared in a high yield and therefore, the superoxide-elimination activity-yield index is likewise very high. As will be seen from this index, the present invention permits the preparation of an extract, having a strong active oxygen-elimination function, from a natural material under the same conditions.

<Evaluation Method of Hydroxyl Radical-Elimination Activity>

The hydroxyl radical-elimination activity was determined as follows: The reaction system used in this example is based on the method, which comprises the steps of generating hydroxyl radicals by a Fenton's reaction, reacting the hydroxyl radicals thus generated with a fatty acid to thus generate malondialdehyde (MDA), reacting MDA with thiobarbituric acid to form a thiobarbituric acid-MDA adduct and then detecting the resulting adduct. More specifically, a solution of a subject to be determined in a desired concentration was dissolved in 0.46 mL of 30 mM Tris-HCl buffer containing a linoleic acid solution (2 mg/mL) and sodium dodecylsulfate (SDS, 2 mg/mL), followed by addition of 0.02 mL of a 2.5 mM hydrogen peroxide solution and 0.02 mL of a 2.5 mM iron(II) chloride solution and warming the resulting mixture at 37° C. for 5 hours. Separately, the same reactions used above were repeated except for omitting the use of the extract, concentrate and purified product thereof to give a control. After warming, 0.01 mL of a 10 mg/mL butyl hydroxytoluene (BHT) ethanol solution was added to the reaction system. TBA (12 mg) and SDS (16.2 mg) were dissolved in 2.3 mL of distilled water, followed by addition of 1.5 mL of 20% (v/v) acetate buffer (pH 4.0) and 0.2 mL of the foregoing reaction solution to the resulting solution and warming the mixture at 95° C. for one hour. After allowing the mixture to cool, the absorbance at 532 nm was determined. The absorbance of the reaction solution containing each sample was defined to be J, that of the control was defined to be K and the rate of hydroxyl radical-elimination thereof were calculated according to the following relation: <Formula 11>. In this respect, it should be recognized that the higher the rate of hydroxyl radical-elimination, the stronger the hydroxyl radical-elimination action.

Rate of Hydroxyl Radical-Elimination(%)=[1−(K−J)/K]×100  <Formula 11>

The intensities of hydroxyl radical-elimination activities are compared with one another by comparing the concentrations of subject to be examined required for achieving the foregoing rate of hydroxyl radical-elimination (%) of 50%.

TABLE 2

| Ex. No. | Raw Material | Extract | Yield (%) | Concn. of test sample required for reducing the rate of hydroxy radical-elimination to 50% (mg/mL) |
|---|---|---|---|---|
| 1 | Defatted Lees 1 | 60%: H₂O—EtOH | 49.2 | 0.69 |
| 1* | Sesame Defatted Lees | 60%: H₂O—EtOH | 11.1 | 0.65 |

"%" appearing in the column entitled "Extract" represents the content of solvent in terms of "% by mass".
Defatted Lees 1: This is prepared by removing seeds from dried fruits of native olive and then subjecting them to the removal of fats.
*Comparative Example The data listed in Table 2 indicate that the extract of the present invention also has a hydroxy radical-elimination activity almost identical to that of the extract derived from sesame seeds, which has been recognized to be one having a strong hydroxy radical-elimination activity. Moreover, when comparing the superoxide-elimination activity of the extract of the invention with that of the extract derived from sesame seeds, the former is about 8 to 9 times that of the latter. Thus, the extract of the present invention is one simultaneously having a strong superoxide-elimination activity and a strong hydroxy radical-elimination activity or an excellent active oxygen-elimination function.

<Evaluation Method of Melanin-Production-Inhibitory Function>

A culture medium was dispensed to wells of a 6-well plate (2 ml/well each), followed by inoculation of a desired amount of B-16 melanoma cells on each well, allowing the wells to stand at 37° C. and 5% CO₂ to thus cultivate the cells. On the day subsequent thereto, a sample (each of a variety of extracts derived from olive) solution prepared was added to the wells with stirring and the cultivation was then continued. The culture medium was replaced with fresh one on the 5th day from the initiation of the cultivation and the sample solution was again added to the wells. On the next day, the culture medium was removed to recover the cells, followed by washing them with PBS (phosphate buffered physiological saline) and then evaluation of the cell-whitening degree. In this respect, the melanin-production-inhibitory function was evaluated by comparing the cell-whitening degree thus obtained with that observed when the same procedures used above were repeated except that 300 μg/ml of arbutin solution (positive control) was substituted for the sample solution used above and that observed when the same procedures used above were repeated except that any sample was not added (control), according to the following evaluation criteria.

The evaluation criteria for the cell-whitening degree are as follows:

++: The cell-whitening degree is higher than that observed for the positive control.

+: The cell-whitening degree is almost identical to that observed for the positive control.

±: The cell-whitening degree is not higher than that observed for the positive control, but is higher than that observed for the control.

−: The cell-whitening degree is almost identical to that observed for the control.

The rate of cell-survival can be calculated according to the aforementioned relation: <Formula 5>.

The melanin-production-inhibitory function was evaluated according to the method described above.

Moreover, the melanin-production-inhibitory function index, substantial melanin-production-inhibitory function index, melanin-production-inhibitory function-yield index and substantial melanin-production-inhibitory function-yield index were calculated according to the foregoing relations: <Formula 3>, <Formula 6>, <Formula 7> and <Formula 8>, respectively.

TABLE 3

| Ex. No. | Concentration (ppm) | | | | | | | |
|---|---|---|---|---|---|---|---|---|
| | 25 | 30 | 50 | 75 | 100 | 150 | 200 | 300 |
| 1 | | | | | −; 100 | ±; 100 | ±; 100 | ±; 100 |
| 2 | | | | | −; 100 | | ±; 100 | ±; 100 |
| 3 | | | | | −; 100 | | ±; 100 | ±; 100 |
| 4 | | | | | −; 100 | | −; 100 | ±; 100 |
| 5 | | | | | | | −; 100 | −; 100 |
| 7 | | | | | −; 100 | | ±; 100 | +; 100 |
| 12 | | | | | −; 100 | | ±; 100 | ±; 100 |
| 13 | | | | | −; 100 | | −; 100 | ±; 77 |
| 14 | −; 100 | −; 100 | ±; 100 | +; 100 | ++; 100 | ++; 100 | ++; 100 | ++; 100 |
| 15 | −; 100 | −; 100 | ±; 100 | +; 100 | ++; 100 | ++; 100 | ++; 100 | ++; 100 |
| 16 | −; 100 | −; 100 | ±; 100 | +; 100 | ++; 100 | ++ | ++; 100 | ++; 100 |
| 18 | ±; 100 | +; 100 | ++; 100 | ++; 100 | ++; 100 | | ++; 100 | ++; 100 |
| 19 | ±; 100 | +; 100 | ++; 100 | ++; 100 | ++; 100 | | ++; 100 | ++; 100 |
| 1* | | | | | −; 100 | | | −; 100 |
| 3* | −; 100 | −; 100 | −; 100 | −; 100 | −; 100 | −; 100 | ±; 100 | ±; 100 |
| 4* | −; 100 | 100 | ±; 100 | ±; 100 | ±; 100 | ±; 100 | ±; 100 | +; 95 |

| Ex. No. | Concentration (ppm) | | | | | | |
|---|---|---|---|---|---|---|---|
| | 400 | 450 | 500 | 600 | 900 | 1000 | 1200 |
| 1 | +; 100 | ++; 100 | ++; 100 | ++; 100 | ++; 58 | ++; 21 | N.D. |
| 2 | +; 100 | ++; 100 | ++; 100 | ++; 100 | ++; 92 | N.D. | |
| 3 | +; 100 | ++; 100 | ++; 100 | ++; 100 | ++; 30 | N.D. | |
| 4 | ±; 100 | ±; 100 | +; 100 | ++; 100 | ++; 77 | ++; 30 | N.D. |
| 5 | ±; 100 | ±; 100 | ±; 100 | +; 100 | +; 64 | ++; 26 | N.D. |
| 6 | | | | | ±; 100 | +; 100 | |
| 7 | ++; 100 | ++; 100 | ++; 100 | ++; 96 | ++; 46 | N.D. | |
| 12 | +; 100 | ++; 100 | ++; 100 | ++; 100 | ++; 81 | ++; 38 | N.D. |
| 13 | ±; 67 | +; 60 | ++; 55 | ++; 44 | ++; 21 | ++; 14 | N.D. |
| 14 | ++; 100 | ++; 100 | ++; 100 | ++; 92 | ++; 36 | ++; N.D. | |
| 15 | ++; 100 | ++; 100 | ++; 100 | ++; 100 | ++; N.D. | | |
| 16 | ++; 100 | ++; 100 | ++; 100 | ++; 100 | ++; 35 | N.D. | |
| 18 | ++; 89 | ++; 22 | N.D. | | | | |
| 19 | ++; 95 | ++; 36 | N.D. | | | | |
| 1* | −; 99 | ±; 100 | ±; 98 | +; 95 | ++; 90 | N.D. | |
| 3* | ±; 100 | ±; 100 | ±; 100 | +; 100 | | | |
| 4* | ++; 81 | ++; 66 | ++; 23 | N.D. | | | |

N.D.: This means that the rate of cell survival is not more than 10%.
The concentration of arbutin as a standard of the cell-whitening degree is 300 ppm. The concentration of arbutin at N.D. is 500 ppm.
*Comparative Example; Comparative Examples 1 to 3 relate to extracts of sesame defatted lees, vitamin C-calcium phosphate and kojic acid, respectively.

N.D.: This means that the rate of cell survival is not more than 10%.

The concentration of arbutin as a standard of the cell-whitening degree is 300 ppm. The concentration of arbutin at N.D. is 500 ppm.

*: Comparative Example; Comparative Examples 1 to 3 relate to extracts of sesame defatted lees, vitamin C-calcium phosphate and kojic acid, respectively.

TABLE 4

| Ex. No. | Raw Material | Solvent | Con. | Yield (%) |
|---|---|---|---|---|
| 1 | Defatted Lees 1 | 40% $H_2O$—EtOH | | 42.9 |
| 2 | Defatted Lees 1 | 20% $H_2O$—EtOH | | 34.8 |
| 3 | Defatted Lees 1 | 30% $H_2O$—EtOH | | 42.7 |

TABLE 4-continued

| | | | | |
|---|---|---|---|---|
| 4 | Defatted Lees 1 | 50% $H_2O$—EtOH | | 48.5 |
| 5 | Defatted Lees 1 | 60% $H_2O$—EtOH | | 49.3 |
| 6 | Defatted Lees 1 | 80% $H_2O$—EtOH | | 48.3 |
| 7 | Defatted Lees 1 | Anhydrous EtOH | | 5.9 |
| 12 | Fruit (free of seeds) | 40% $H_2O$—EtOH | | 12.6 |
| 13 | Seeds | 35% $H_2O$—EtOH | | 8.4 |
| 14 | Defatted Lees 2 | 40% $H_2O$—EtOH | | 9.8 |
| 15 | Defatted Lees 2 | 30% $H_2O$—EtOH | | 8.9 |
| 16 | Defatted Lees 3 | 40% $H_2O$—EtOH | | 4.5 |
| 18 | Defatted Lees 1 | 40% $H_2O$—EtOH | Free of Easily Water-Soluble Fraction | 4.9 |
| 19 | Defatted Lees 2 | 40% $H_2O$—EtOH | Free of Easily Water-Soluble Fraction | 5.0 |
| 1* | Sesame Defatted Lees | 40% $H_2O$—EtOH | | 11.1 |
| 3* | Vitamin C-$Mg_3(PO_4)_2$ | — | | — |
| 4* | Kojic Acid | — | | — |

| Ex. No. | MPIF Index[1] | Substantial MPIF Index[2] | MPIF-Y Index | Substantial MPIF-Y Index |
|---|---|---|---|---|
| 1 | 1.0 | 2.4 | 49.2 | 118.1 |
| 2 | 1.0 | 2.0 | 34.8 | 69.6 |
| 3 | 1.0 | 2.0 | 42.7 | 85.4 |
| 4 | 0.8 | 1.8 | 36.4 | 87.3 |
| 5 | 0.6 | 1.4 | 29.6 | 71.0 |
| 6 | 0.5 | 1.5 | 24.2 | 72.5 |
| 7 | 1.2 | 2.4 | 7.1 | 14.2 |
| 12 | 1.0 | 2.4 | 12.6 | 30.2 |
| 13 | 0.7 | 1.6 | 5.6 | 13.4 |
| 14 | 4.0 | 8.0 | 39.2 | 78.4 |
| 15 | 4.0 | 7.2 | 35.6 | 64.1 |
| 16 | 4.0 | 8.0 | 18.0 | 36.0 |
| 18 | 10.0 | 10.0 | 49.0 | 49.0 |
| 19 | 10.0 | 10.0 | 50.0 | 50.0 |
| 1* | 0.3 | 0.7 | 3.7 | 7.4 |
| 3* | 0.5 | — | — | — |
| 4* | 1.0 | 1.2 | — | — |

Defatted Lees 1: This is prepared by removing seeds from dried fruits of native olive and then subjecting them to the removal of fats.
Defatted Lees 2: This is prepared by removing seeds from pressed residue of olive native of Italy and then subjecting it to the removal of fats.
Defatted Lees 3: This is prepared by subjecting pressed residue of olive native of Italy to the removal of fats (including seeds).
*Comparative Example; MPIF Index: Melanin-production-inhibitory function index; Substantial MPIF Index: Substantial melanin-production-inhibitory function index; MPIF-Y Index: Melanin-production-inhibitory function-yield index; Substantial MPIF-Y Index: Substantial melanin-production-inhibitory function-yield index.

The results obtained in Examples listed in Tables 3 and 4 indicate that the extract of the present invention (even in the simple extract derived from a natural material free of any post-treatment) has a melanin-production-inhibitory function identical or superior to those observed for arbutin and kojic acid, which have been known to be whitening agents having a high whitening effect and an excellent melanin-production-inhibitory function, and has a quite strong melanin-production-inhibitory function considerably higher than that of vitamin C-magnesium phosphate. Moreover, the extract of the invention also has a low toxicity and therefore, it is found that the substantial melanin-production-inhibitory function thereof is higher than that of arbutin. Accordingly, it is found that the extract shows a quite excellent whitening effect when it is practically applied to the skin.

In addition, it is clear from the comparison of Examples 1 and 14 with Comparative Example 1 that the extract of the invention has a strong melanin-production-inhibitory function and can be prepared from a raw material under the same conditions in a high yield and thus the melanin-production-inhibitory function-yield index and the substantial melanin-production-inhibitory function-yield index thereof are considerably higher than those observed for extracts derived from other natural substances.

Moreover, the results obtained in Examples 18 and 19 indicate that the melanin-production-inhibitory function of the extract of the invention can be considerably improved by concentration. In these Examples, the extract is concentrated by the method, which comprises removing the easily water-soluble fraction thereof while making use of the solubility thereof in water. This extract has a very high melanin-production-inhibitory effect on the skin on the order of 10 times that observed for arbutin.

Then the skin-beautifying effect of the extract was evaluated by actually formulating a variety of agents externally applied to the skin such as a cream, a toilet water and a milky lotion to which the extract of the invention was added and applying the resulting external agent for the skin to the skin of female panelists. In particular, the anti-aging effect for the skin and the whitening effect of the extract were evaluated. Methods for the evaluation thereof and the results thus obtained will be detailed below.

Example 20

Cream

Creams each having the composition specified in the following Table 5 were prepared using the extracts prepared in the foregoing Examples according to the method detailed below and the resulting creams were inspected for the anti-aging effect for the skin. The results thus obtained are also listed in Table 5.

TABLE 5

| Component (%) | Present Invention | | | | | | Comp. Ex. | |
|---|---|---|---|---|---|---|---|---|
| | 1 | 2 | 3 | 4 | 5 | 6 | 1 | 2 |
| (1) Bees Wax | 6.0 | 6.0 | 6.0 | 6.0 | 6.0 | 6.0 | 6.0 | 6.0 |
| (2) Cetanol | 5.0 | 5.0 | 5.0 | 5.0 | 5.0 | 5.0 | 5.0 | 5.0 |
| (3) Reduced Lanolin | 5.0 | 5.0 | 5.0 | 5.0 | 5.0 | 5.0 | 5.0 | 5.0 |
| (4) Squalane | 30.0 | 30.0 | 30.0 | 30.0 | 30.0 | 30.0 | 30.0 | 30.0 |
| (5) Glycerin Monostearate | 4.0 | 4.0 | 4.0 | 4.0 | 4.0 | 4.0 | 4.0 | 4.0 |
| (6) Lipophilic Glycerin Monostearate | 2.0 | 2.0 | 2.0 | 2.0 | 2.0 | 2.0 | 2.0 | 2.0 |
| (7) POE-sorbitan monolauric acid ester | 2.0 | 2.0 | 2.0 | 2.0 | 2.0 | 2.0 | 2.0 | 2.0 |

TABLE 5-continued

|  | Present Invention | | | | | | Comp. Ex. | |
|---|---|---|---|---|---|---|---|---|
| Component (%) | 1 | 2 | 3 | 4 | 5 | 6 | 1 | 2 |
| (20 E.O.) | | | | | | | | |
| (8) Extract of Ex. 1 | 0.25 | | | | | | | |
| (9) Extract of Ex. 3 | | 0.25 | | | | | | |
| (10) Extract of Ex. 5 | | | 0.25 | | | | | |
| (11) Extract of Ex. 13 | | | | 0.25 | | | | |
| (12) Extract of Ex. 14 | | | | | 0.25 | | | |
| (13) Extract of Ex. 16 | | | | | | 0.25 | | |
| (14) Extract of Comp. Ex. 1 | | | | | | | 0.25 | |
| (15) Preservative | 0.2 | 0.2 | 0.2 | 0.2 | 0.2 | 0.2 | 0.2 | 0.2 |
| (16) Perfume | q.s. (as much as suffices) | | | | | | | |
| (17) Purified Water | Balance | | | | | | | |
| Aging-aging Effect Effective | 11 | 13 | 10 | 9 | 9 | 8 | 4 | 0 |
| Slightly Effective | 4 | 2 | 5 | 5 | 5 | 6 | 4 | 3 |
| Not effective | 0 | 0 | 0 | 1 | 1 | 1 | 7 | 12 |

(Preparation Method)

A. The components (1) to (6) and (15) were mixed, heated to 70° C. and then maintained at that temperature.

B. The components (7) to (14) and (17) were admixed together, heated to 70° C. and then maintained at that temperature.

C. The mixture B was added to the mixture A, followed by mixing them.

D. The component (16) was added to the foregoing mixture with cooling to give a cream.

(Test Method)

An appropriate amount of each cream to be tested was applied to the faces of female panelists (15 panelists of 20-year-old to 54-year-old per test cream) twice a day in the morning and evening every day over 8 weeks, after washing the faces. The anti-aging effect for the skin of each test cream thus applied to the face was evaluated according to the following evaluation criteria:

(Evaluation Criteria)

| Rank | Details |
|---|---|
| Effective | The test sample imparts tenseness and gloss to the skin and relieves wrinkles and sags. |
| Slightly Effective | The test sample slightly imparts tenseness and gloss to the skin and slightly relieves wrinkles and sags. |
| Not Effective | The conditions of the skin are almost identical to those observed before the test sample is applied. |

From the results listed in the following Table 5, it has been proved that the creams 1 to 6 containing the extract of the present invention can impart tenseness and gloss to the skin, can relieve wrinkles and sags and can make the skin beautiful.

Accordingly, it has been proved that the creams 1 to 6 containing the extract of the present invention possess an excellent anti-aging effect for the skin.

Example 21

Cream

Creams each having the composition specified in the following Table 6 were prepared using the extracts prepared in the foregoing Examples according to the method detailed below and the resulting creams were inspected for the whitening effect. The results thus obtained are also listed in Table 6.

TABLE 6

|  | Product of the present Invention | | | | |
|---|---|---|---|---|---|
| Component (%) | 1 | 2 | 3 | 4 | 5 |
| (1) Bees Wax | 6.0 | 6.0 | 6.0 | 6.0 | 6.0 |
| (2) Cetanol | 5.0 | 5.0 | 5.0 | 5.0 | 5.0 |
| (3) Reduced Lanolin | 5.0 | 5.0 | 5.0 | 5.0 | 5.0 |
| (4) Squalane | 30.0 | 30.0 | 30.0 | 30.0 | 30.0 |
| (5) Glycerin Monostearate | 4.0 | 4.0 | 4.0 | 4.0 | 4.0 |
| (6) Lipophilic Glycerin Monostearate | 2.0 | 2.0 | 2.0 | 2.0 | 2.0 |
| (7) POE Sorbitan Monolauric Acid Ester (20 E.O.) | 2.0 | 2.0 | 2.0 | 2.0 | 2.0 |
| (11) Extract of Ex. 1 | 0.05 | | | | |
| (12) Extract of Ex. 13 | | 0.05 | | | |
| (13) Extract of Ex. 14 | | | 0.05 | | |
| (14) Extract of Ex. 16 | | | | 0.05 | |
| (15) Extract of Ex. 19 | | | | | 0.05 |
| (17) Preservative | 0.2 | 0.2 | 0.2 | 0.2 | 0.2 |
| (18) Perfume | q.s. (as much as suffices) | | | | |
| (19) Purified water | Balance | | | | |
| Whitening Effect Effective | 9 | 8 | 12 | 12 | 15 |
| Slightly Effective | 4 | 5 | 3 | 3 | 0 |
| Not Effective | 2 | 2 | 0 | 0 | 0 |

|  | Comparative Product | | | | |
|---|---|---|---|---|---|
| Component (%) | 1 | 2 | 3 | 4 | 5 |
| (1) Bees Wax | 6.0 | 6.0 | 6.0 | 6.0 | 6.0 |
| (2) Cetanol | 5.0 | 5.0 | 5.0 | 5.0 | 5.0 |
| (3) Reduced Lanolin | 5.0 | 5.0 | 5.0 | 5.0 | 5.0 |
| (4) Squalane | 30.0 | 30.0 | 30.0 | 30.0 | 30.0 |
| (5) Glycerin Monostearate | 4.0 | 4.0 | 4.0 | 4.0 | 4.0 |
| (6) Lipophilic Glycerin Monostearate | 2.0 | 2.0 | 2.0 | 2.0 | 2.0 |
| (7) POE Sorbitan Monolauric Acid Ester (20 E.O.) | 2.0 | 2.0 | 2.0 | 2.0 | 2.0 |
| (8) Vitamin C-Magnesium Phosphate | 0.05 | | | | |
| (9) Kojic Acid | | 0.05 | | | |
| (10) Arbutin | | | 0.05 | | |
| (16) Extract of Comp. Ex. 1 | | | | 0.05 | |
| (17) Preservative | 0.2 | 0.2 | 0.2 | 0.2 | 0.2 |
| (18) Perfume | q.s. (as much as suffices) | | | | |
| (19) Purified Water | Balance | | | | |
| Whitening Effect Effective | 5 | 9 | 9 | 4 | 0 |
| Slightly Effective | 7 | 4 | 3 | 6 | 1 |
| Not Effective | 3 | 2 | 3 | 5 | 14 |

(Preparation Method)
A. The components (1) to (6) and (17) were admixed together, heated to 70° C. and then maintained at that temperature.
B. The components (7) to (16) and (19) were admixed together, heated to 70° C. and then maintained at that temperature.
C. The mixture A was added to and mixed with the mixture B.
D. The component (16) was added to the resulting mixture with cooling to give a cream.

(Test Method)
An appropriate amount of each cream to be tested was applied to the faces of female panelists (15 panelists of 27-year-old to 54-year-old per test cream) twice a day in the morning and evening every day over 12 weeks, after washing the faces. The whitening effect of each test cream thus applied to the face was evaluated according to the following evaluation criteria:

| (Evaluation Criteria) | | |
|---|---|---|
| Rank | Details | |
| Effective | The test sample makes dark skin, melasma, ephelis and dullness inconspicuous. | |
| Slightly Effective | The test sample makes dark skin, melasma, ephelis and dullness inconspicuous to some extent. | |
| Not Effective | The conditions of the skin are almost identical to those observed before the test sample is applied. | |

From the results listed in the foregoing Table 6, it has been proved that the creams 1 to 5 containing the extract of the present invention can reduce or prevent the generation of, for instance, any "dullness" on the skin and can make the skin beautiful.

Accordingly, it has been proved that the creams 1 to 5 containing the extract of the present invention possess a whitening effect higher than those observed for the extracts containing, for instance, arbutin, kojic acid and vitamin C-magnesium phosphate.

Example 22

Toilet Water

A toilet water having the following formulation was prepared according to the method specified below.

| Formulation | (%) |
|---|---|
| (1) Glycerin | 5.0 |
| (2) 1,3-Butylene Glycol | 6.5 |
| (3) Polyoxyethylene (20 E.O.) Sorbitan Monolauric Acid Ester | 1.2 |
| (4) Ethanol | 8.0 |
| (5) Extract of Ex. 1 | 3.0 |
| (6) Preservative | q.s. |
| (7) Perfume | q.s. |
| (8) Purified Water | Balance |

(Preparation Method)
A. The components (3), (4), (6) and (7) were admixed and dissolved together.
B. The components (1), (2), (5) and (8) were admixed and dissolved together.
C. The mixtures A and B were uniformly admixed together to form a toilet water.

Example 23

Milky Lotion

A milky lotion having the following formulation was prepared according to the following method.

| Formulation | (%) |
|---|---|
| (1) Polyoxyethylene (10 E.O.) Sorbitan Monostearate | 1.0 |
| (2) Polyoxyethylene (60 E.O.) Sorbit Tetraoleate | 0.5 |
| (3) Glyceryl Monostearate | 1.0 |
| (4) Stearic Acid | 0.5 |
| (5) Behenyl Alcohol | 0.5 |
| (6) Squalane | 8.0 |
| (7) Extract of Example 10 | 0.05 |
| (8) Preservative | 0.1 |
| (9) Carboxy Vinyl Polymer | 0.1 |
| (10) Sodium Hydroxide | 0.05 |
| (11) Ethyl Alcohol | 5.0 |
| (12) Purified Water | Balance |
| (13) Perfume | q.s. |

(Preparation Method)
A. The components (8) to (12) were admixed together with heating and the resulting mixture was maintained at 70° C.
B. The components (1) to (6) were admixed together with heating and the resulting mixture was maintained at 70° C.
C. The mixture A was added to and mixed with the mixture B to thus give a uniform emulsion.
D. After cooling the product C, the components (7) and (13) were added thereto and uniformly admixed together to give a milky lotion.

Example 24

Cream

A cream having the following formulation was prepared according to the following method.

| Formulation | (%) |
|---|---|
| (1) Polyoxyethylene (40 E.O.) Monostearate | 2.0 |
| (2) Glycerin Monostearate (self-emulsifiable type one) | 5.0 |
| (3) Stearic Acid | 5.0 |
| (4) Behenyl Alcohol | 0.5 |
| (5) Squalane | 15.0 |
| (6) Cetyl Isooctanoate | 5.0 |
| (7) Butyl Paraben | 0.1 |
| (8) Methyl Paraben | 0.1 |
| (9) 1,3-Butylene Glycol | 5.0 |
| (10) Extract of Example 12 | 0.05 |
| (11) Purified Water | Balance |
| (12) Perfume | q.s. |

(Preparation Method)
A. The components (1) to (7) were heated to 70° C. to dissolve the same.
B. The components (8) to (11) were heated to 70° C.
C. The mixture A was added to the mixture B and the component (12) was added to the resulting mixture with cooling to give a cream.

It has been proved that all of the toilet water of Example 22, the milky lotion of Example 23 and the cream of Example 24 are excellent in stability with time, that the application thereof to the skin can impart tenseness and gloss to the skin, permits the alleviation of wrinkles and sags and simultaneously prevent any occurrence of, for instance, "dullness" of the skin, that they can reduce the deposition of pigments such as melasma and that they can make the skin transparent and beautiful.

Example 25

Pack

A pack having the following formulation was prepared according to the following method.

| Formulation | (%) |
|---|---|
| (1) Polyvinyl Alcohol | 20.0 |
| (2) Ethanol | 20.0 |
| (3) Glycerin | 5.0 |
| (4) Kaolin | 6.0 |
| (5) Extract of Example 9 | 0.5 |
| (6) Preservative | q.s. |
| (7) Perfume | q.s. |
| (8) Purified Water | Balance |

(Preparation Method)

A. The components (1), (3), (4) and (8) were admixed together, the resulting mixture was heated to 70° C. and then stirred.
B. The components (2), (6) and (7) were admixed together.
C. The foregoing mixture B was added to and mixed with the foregoing mixture A and then the component (5) was uniformly dispersed in the resulting mixture with cooling to thus give a pack.

It has been proved that the pack thus prepared is excellent in stability with time, that the application thereof to the skin can impart tenseness and gloss to the skin, permits the alleviation of wrinkles and sags, and simultaneously conditions the texture of the skin, prevent any occurrence of, for instance, "dullness" of the skin and can reduce the deposition of pigments such as melasma and that it can make the skin transparent and beautiful.

Example 26

Liquid Foundation

A liquid foundation having the following formulation was prepared according to the following method.

| Formulation | (%) |
|---|---|
| (1) Lanolin | 7.0 |
| (2) Liquid Paraffin | 5.0 |
| (3) Stearic Acid | 2.0 |
| (4) Cetanol | 1.0 |
| (5) Glycerin | 5.0 |
| (6) Triethanolamine | 1.0 |
| (7) Carboxy Methyl Cellulose | 0.7 |
| (8) Purified Water | Balance |
| (9) Mica | 15.0 |
| (10) Talc | 6.0 |
| (11) Titanium Oxide | 3.0 |
| (12) Coloring Pigment | 6.0 |
| (13) Extract of Example 1 | 0.05 |
| (14) Ultraviolet Screening Agent | q.s. |
| (15) Perfume | q.s. |

(Preparation Method)

A. The components (1) to (4) were mixed and dissolved together.
B. The components (9) to (12) were added to and uniformly admixed with the foregoing mixture A.
C. The components (5) to (8) were uniformly dissolved together and the resulting mixture was maintained at 70° C.
D. The foregoing mixture C was added to and uniformly admixed with the foregoing mixture B to give an emulsion.
E. After cooling the foregoing mixture D, the components (13) to (15) were added thereto to give a liquid foundation.

It was found that the liquid foundation prepared in Example 26 was excellent in stability with time and that the application thereof to the skin could prevent the occurrence of any "wrinkle" due to, for instance, sunburn. Moreover, it was also found that the application thereof could impart tenseness and gloss to the skin and could alleviate wrinkles and sags. Further it was also found that the liquid foundation could prevent the darkening and the generation of melasma due to sunburn.

Example 27

Sunscreen Milky Lotion

A sunscreen milky lotion having the following formulation was prepared according to the method detailed below.

| Formulation | (%) |
|---|---|
| (1) Stearic Acid | 2.0 |
| (2) Cetanol | 1.0 |
| (3) Polyoxyethylene sorbitan monooleate (20 E.O.) | 0.5 |
| (4) Sorbitan Sesqui-oleate | 0.5 |
| (5) 2-ethylhexyl p-Methoxy Cinnamate | 8.0 |
| (6) Cetyl 2-Ethylhexanoate | 12.0 |
| (7) 1,3-Butylene Glycol | 10.0 |
| (8) Carboxy Vinyl Polymer | 0.2 |
| (9) Triethanolamine | 0.5 |
| (10) Extract of Example 3 | 0.25 |
| (11) Purified Water | Balance |
| (12) Preservative | q.s. |
| (13) Titanium Oxide | 3.0 |
| (14) Perfume | q.s |

(Preparation Method)

A. The components (1) to (6) were mixed together with heating and the resulting mixture was maintained at 75° C.
B. The components (7) to (12) were mixed together with heating and the resulting mixture was maintained at 75° C.
C. The foregoing mixture A was gradually added to the mixture B.
D. The components (13) to (14) were added to the resulting mixture C while cooling the latter to give a sunscreen milky lotion.

The sunscreen milky lotion prepared in Example 27 was found to be excellent in the stability with time and the application thereof to the skin could prevent the generation of any "wrinkle" due to, for instance, sunburn. Moreover, it was proved that the milky lotion could impart tenseness and gloss to the skin and that it could likewise relieve lighten wrinkles and sags.

Example 28

Sunscreen Milky Lotion

A sunscreen milky lotion having the following formulation was prepared according to the method detailed below.

| Formulation | (%) |
| --- | --- |
| (1) Stearic Acid | 2.0 |
| (2) Cetanol | 1.0 |
| (3) Polyoxyethylene sorbitan monooleate (20 E.O.) | 0.5 |
| (4) Sorbitan Sesqui-oleate | 0.5 |
| (5) 2-ethylhexyl p-Methoxy Cinnamate | 8.0 |
| (6) Cetyl 2-Ethylhexanoate | 12.0 |
| (7) 1,3-Butylene Glycol | 10.0 |
| (8) Carboxy Vinyl Polymer | 0.2 |
| (9) Triethanolamine | 0.5 |
| (10) Extract of Example 14 | 0.05 |
| (11) Purified Water | Balance |
| (12) Preservative | q.s. |
| (13) Titanium Oxide | 3.0 |
| (14) Perfume | q.s |

(Preparation Method)
A. The components (1) to (6) were mixed together with heating and the resulting mixture was maintained at 75° C.
B. The components (7) to (12) were mixed together with heating and the resulting mixture was maintained at 75° C.
C. The foregoing mixture A was gradually added to the mixture B.
D. The components (13) to (14) were added to the resulting mixture C while cooling the latter to give a sunscreen milky lotion.

It was found that the sunscreen milky lotion prepared in Example 28 was excellent in the stability with time and that the application thereof to the skin could prevent the occurrence of any dark skin and melasma due to, for instance, sunburn.

Example 29

Gel Ointment

A gel ointment having the formulation specified below was prepared according to the method detailed below.

| Formulation | (%) |
| --- | --- |
| (1) Carboxyvinyl Polymer | 1.0 |
| (2) Triethanolamine | 1.0 |
| (3) 1,3-Butylene Glycol | 10.0 |
| (4) Extract prepared in Example 10 | 0.05 |
| (5) Purified Water | Balance |

(Preparation Method)
A. The components (1) and (3) to (5) were admixed and dissolved together.
B. The component (2) was added to the resulting mixture A and uniformly mixed together to give a gel ointment.

It has been proved that the gel ointment prepared in Example 29 is excellent in stability with time, that the application thereof to the skin can impart tenseness and gloss to the skin, permits the alleviation of wrinkles and sags, and can simultaneously condition the texture of the skin, prevent any occurrence of, for instance, "dullness" of the skin and reduce the deposition of pigments such as melasma and that it can make the skin transparent and beautiful.

The present invention thus permits the preparation of an external agent for the skin having a skin-beautifying effect, in particular, an excellent anti-aging effect for the skin or an effect of imparting tenseness and gloss to the skin and of preventing the formation of any wrinkle and sag and an excellent whitening effect or an effect of preventing the occurrence of any dark skin, melasma, ephelis and dullness of the skin and also permits the preparation of an external agent for the skin, which is stable, safe to the human body and excellent in the storage stability.

Moreover, the skin-beautifying agent, the anti-aging agent and the whitening agent containing the extracts derived from olive plants as effective components can directly be applied to the skin to thus ensure strong skin-aging-inhibitory and whitening effects or may be used as raw materials for agents externally applied to the skin.

Furthermore, the extract of the invention can easily be prepared from olive plants and can likewise suitably be prepared from products generated during or after the olive oil-manufacturing process, which are usually discarded as wastes and therefore, the present invention is advantageous from the viewpoint of the production cost, the stable supply of the extract and the effective use of resources.

What is claimed is:

1. An external agent for the skin comprising an extract derived by defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

2. The external agent for the skin of claim 1 wherein it further comprises at least one effective drug selected from the group consisting of a whitening agent, an antioxidant, an anti-inflammatory agent, a cell-activator, a ultraviolet-screening agent, a blood-circulation promoter and a humectant.

3. The external agent for the skin of claim 1 wherein the water insoluble organic solvent is selected from the group consisting of pentane, hexane, heptane, ethylacetate and diethylether and the water-containing hydrophilic organic solvent is water-containing alcohol.

4. The external agent for the skin of claim 3 wherein the water-containing alcohol has an alcohol content ranging from 10 to 95% by mass and the alcohol is one having 1 to 4 carbon atoms.

5. The external agent for the skin of claim 1 wherein the water insoluble organic solvent is hexane and the water-containing hydrophilic organic solvent is water-containing ethanol having an ethanol content ranging from 30 to 95% by mass.

6. A whitening agent for the skin comprising, as an effective component, an extract derived by defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

7. The whitening agent for the skin of claim 6 wherein it further comprises at least one effective drug selected from the group consisting of a whitening agent, an antioxidant, an anti-inflammatory agent, a cell-activator, a ultraviolet-screening agent, a blood-circulation promoter and a humectant.

8. The whitening agent for the skin of claim 6 wherein the water insoluble organic solvent is selected from the group consisting of pentane, hexane, heptane, ethylacetate and diethylether and the water-containing hydrophilic organic solvent is water-containing alcohol.

9. The whitening agent for the skin of claim 8 wherein the water-containing alcohol has an alcohol content ranging from 10 to 95% by mass and the alcohol is one having 1 to 4 carbon atoms.

10. The whitening agent for the skin of claim 6 wherein the water insoluble organic solvent is hexane and the water-containing hydrophilic organic solvent is water-containing ethanol having an ethanol content ranging from 30 to 95% by mass.

11. An anti-aging agent for the skin comprising, as an effective component an extract derived by defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

12. The anti-aging agent for the skin of claim 11 wherein it further comprises at least one effective drug selected from the group consisting of a whitening agent, an antioxidant, an anti-inflammatory agent, a cell-activator, a ultraviolet-screening agent, a blood-circulation promoter and a humectant.

13. The anti-aging agent for the skin of claim 11 wherein the water insoluble organic solvent is selected from the group consisting of pentane, hexane, heptane, ethylacetate and diethylether and the water-containing hydrophilic organic solvent is water-containing alcohol.

14. The anti-aging agent for the skin of claim 13 wherein the water-containing alcohol has an alcohol content ranging from 10 to 95% by mass and the alcohol is one having 1 to 4 carbon atoms.

15. The anti-aging agent for the skin of claim 11 wherein the water insoluble organic solvent is hexane and the water-containing hydrophilic organic solvent is water-containing ethanol having an ethanol content ranging from 30 to 95% by mass.

16. A skin-beautifying agent comprising, as an effective component, an extract derived by defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

17. A method of applying an agent to the skin of a human being, the agent comprising an extract derived by defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

18. A method of whitening the skin of a human being comprising the step of applying an agent to the skin of a human being, the agent comprising an extract derived defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

19. A method of reducing the signs of aging of the skin of a human being comprising the step of applying an agent to the skin of a human being, the agent comprising an extract derived by defatting an olive plant part with a water insoluble organic solvent to obtain a defatted product as a residue, and extracting the defatted residue with a water-containing hydrophilic organic solvent, wherein the olive plant part is selected from the group consisting of fruits, seeds, pericarp, seed coat, leaves, stems or buds.

20. A process for producing an external agent for the skin comprising:

defatting an olive plant part with a water insoluble organic solvent to obtain a defatted product as a residue, extracting the resulting defatted residue with a water-containing hydrophilic organic solvent, filtering the resulting extraction, and concentrating the resulting filtrate to dryness, wherein the olive plant part is selected from the group consisting of fruits, seeds, pericarp, seed coat, leaves, stems or buds.

21. The process of claim 20 wherein the water containing alcohol has an alcohol content ranging from 10 to 95% by mass and the alcohol is one having 1 to 4 carbon atoms.

22. The process of claim 20 further comprising the step of a concentration treatment and/or a fractionation-purification treatment.

* * * * *